(12) United States Patent
Cepko et al.

(10) Patent No.: US 8,912,153 B2
(45) Date of Patent: Dec. 16, 2014

(54) HDAC4 NUCLEIC ACID ADMINISTRATION TO TREAT RETINAL DISEASE

(75) Inventors: Constance L. Cepko, Newton, MA (US); Bo Chen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 643 days.

(21) Appl. No.: 13/058,346

(22) PCT Filed: Aug. 13, 2009

(86) PCT No.: PCT/US2009/053730
§ 371 (c)(1),
(2), (4) Date: May 3, 2011

(87) PCT Pub. No.: WO2010/019786
PCT Pub. Date: Feb. 18, 2010

(65) Prior Publication Data
US 2011/0268705 A1    Nov. 3, 2011

Related U.S. Application Data

(60) Provisional application No. 61/088,455, filed on Aug. 13, 2008.

(51) Int. Cl.
| | | |
|---|---|---|
| *C12N 15/00* | (2006.01) | |
| *A61K 48/00* | (2006.01) | |
| *C07K 14/47* | (2006.01) | |
| *A01K 67/027* | (2006.01) | |
| *C12N 9/16* | (2006.01) | |
| *C12N 15/63* | (2006.01) | |
| *C12N 15/85* | (2006.01) | |
| *C12N 15/67* | (2006.01) | |
| *A61K 39/00* | (2006.01) | |

(52) U.S. Cl.
CPC ............ *C07K 14/4702* (2013.01); *A01K 67/027* (2013.01); *C12N 9/16* (2013.01); *C12N 15/63* (2013.01); *C12N 15/85* (2013.01); *C12N 15/67* (2013.01); *A61K 2039/53* (2013.01); *A01K 2207/05* (2013.01); *A01K 2227/105* (2013.01); *A01K 2267/03* (2013.01); *A61K 48/00* (2013.01); *C12N 2799/025* (2013.01)
USPC ...................... 514/44 R; 435/320.1; 435/455

(58) Field of Classification Search
CPC .... A61K 2039/53; C12N 15/63; C12N 15/67; C12N 15/85; C12N 2799/025
See application file for complete search history.

(56) References Cited

U.S. PATENT DOCUMENTS

2005/0202450 A1   9/2005  Huang et al.
2005/0261234 A1   11/2005 Dorey et al.

OTHER PUBLICATIONS

Bolger et al. Intracellular Trafficking of Histone Deacetylase 4 Regulates Neuronal Cell Death. J. Neuroscience, 2005, vol. 25, pp. 9544-9553.*
Adler et al. Cell death in age-related macular degeneration. Molec. Vision, 1999, vol. 5, pp. 31-37.*
Rhee et al. Molecular and Cellular Alterations Induced by Sustained Expression of Ciliary Neurotrophic Factor in a Mouse Model of Retinitis Pigmentosa. Investi. Opfthalmol.Vis. Sci., 2007, vol. 48, pp. 1380-1400.*
Bolger et al. (2005), "Intracellular Trafficking of Histone Deacetylase 4 Regulates Neuronal Cell Death," J. Neurosci. 25:9544-9553.
Cepko et al. (1998), "Lineage Analysis Using Retroviral Vectors," Curr. Top. Dev. Biol. 36:51-74.
Chen et al. (2007), "Requirement of histone deacetylase activity for the expression of critical photoreceptor genes," Dev Biol. 7:78.
Chang-Chi, et al. (2006), "Effect of Connective Tissue Growth Factor on Hypoxia-Inducible Factor 1α Degradation and Tumor Angiogenesis," J. Natl. Cancer Inst. 98(14):984-995.
Grimm et al. (2002), "HIF-1-induced erythropoietin in the hypoxic retina protects against light-induced retinal degeneration," Nat. Med. 8(7):718-724.
Grozinger et al. (2000), "Regulation of histone deacetylase 4 and 5 and transcriptional activity by 14-3-3-dependent cellular localization," Proc. Natl. Acad. Sci. USA 97(14):7835-7840.
Jeong et al. (2002), "Regulation and Destabilization of HIF-1alpha by ARD1-Mediated Acetylation," Cell 111:709-720.
Jiang et al. (1996), "Dimerization, DNA Binding, and Transactivation Properties of Hypoxia-inducible Factor 1," J. Biol. Chem. 271(30):17771-17778.
Kuo et al. (1998), "Roles of histone acetyltransferases and deacetylases in gene regulation," BioEssays 20:615-626.
Matsuda et al. (2004), "Electroporation and RNA interference in the rodent retina in vivo and in vitro," Proc. Natl. Acad. Sci. USA 101(1):16-22.
Majdzadeh et al. (2008) "HDAC4 Inhibits Cell-Cycle Progression and Protects Neurons from Cell Death," Dev Neurobiol 68(8):1076-1092 268.
Miska et al. (1999), "HDAC4 deacetylase associates with and represses the MEF2 transcription factor," Embo. J. 18(18):5099-5107.
Pandey et al. (2007), "HDAC6 rescues neurodegeneration and provides an essential link between autophagy and the UPS," Nature 447:859-863.
Portera-Cailliau et al. (1994), "Apoptotic photoreceptor cell death in mouse models of retinitis pigmentosa," Proc Natl Acad Sci USA 91:974-978.
Rakoczy et al. (2006), "Mouse models of age-related macular degeneration," Exp. Eye Res. 82(5):741-752.

(Continued)

*Primary Examiner* — Deborah Crouch
(74) *Attorney, Agent, or Firm* — McCarter & English, LLP; Maria Laccotripe Zacharakis; Deborah L. Nagle

(57) ABSTRACT

Methods for inhibiting retinal cell death by altering expression of one or more of HDAC4, HDAC5, HDAC6, HDAC7, and HIF1α in a retinal cell are provided.

20 Claims, 10 Drawing Sheets

(56) References Cited

OTHER PUBLICATIONS

Rajan et al. (2009) "Loss of the Putative Catalytic Domain of HDAC4 Leads to Reduced Thermal Nociception and Seizures while Allowing Normal Bone Development," PLoS ONE 4(8):e6612.

Semenza (2000), "HIF-1: mediator of physiological and pathophysiological responses to hypoxia," J. Appl. Physiol. 88:1474-1480.

Semenza (2006), "Regulation of physiological responses to continuous and intermittent hypoxia by hypoxia-inducible factor1," Exp. Physiol. 91:803-806.

Taymans et al. (2007), "Comparative Analysis of Adeno-Associated Viral Vector Serotypes 1, 2, 5, 7, and 8 in Mouse Brain," Hun. Gene Ther. 18(3):195-206.

Wang et al. (2001), "Histone Deacetylase 4 Possesses Intrinsic Nuclear Import and Export Signals," Mol. Cell. Biol. 21(17):5992-6005.

Xu et al. (2007), "Histone deacetylase inhibitors: molecular mechanisms of action," Oncogene 26, 5541-5552.

Yang et al. (2007), "HATs and HDACs: from structure, function and regulation to novel strategies for therapy and prevention," Oncogene 26, 5310-5318.

Young et al. (1984), "Cell Death During Differentiation of the Retina in the Mouse," J Comp Neurol 229, 362-373.

Zhao et al. (2001), "The Modular Nature of Histone Deacetylase HDAC4 Confers Phosphorylation-dependent Intracellular Trafficking," J. Biol. Chem. 276(37):35042-35048.

* cited by examiner

_US 8,912,153 B2_

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggagatgctg gccatgaagc a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 2
ggaaatgcta gctatgaaac a                                              21

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide for blocking HDAC4

<400> SEQUENCE: 3

Met Ser Ser Gln Ser His Pro Asp Gly Leu Ser Gly Arg Asp Gln
  1               5                  10                  15

Pro Val Glu Leu
```

HDAC4 NUCLEIC ACID ADMINISTRATION TO TREAT RETINAL DISEASE

RELATED APPLICATIONS

This application claims priority to U.S. Provisional Application No. 61/088,455, filed on Aug. 13, 2008, the entire contents of which are incorporated herein by this reference.

STATEMENT OF GOVERNMENT INTERESTS

This invention was made with government support under EY09676 awarded by the National Institutes of Health. The United States Government has certain rights in the invention.

FIELD OF THE INVENTION

The present invention relates to neurodegenerative diseases such as, for example, retinal degenerations.

BACKGROUND OF THE INVENTION

Vision loss and blindness due to retinal cell death is a severe problem. In a 2004 publication, the World Health Organization (WHO) estimated that the global population of blind and visually impaired persons was over 300 million, with almost 10 million in the United States (WHO Bulletin 82 pp 844-851—Global Data on Visual Impairment November, 2004). The major cause of blindness among the elderly in the developed world is age-related macular degeneration (AMD), which is estimated to cause half of all blindness cases in the U.S. AMD gradually destroys sharp central vision, which is needed for activities such as driving and reading. AMD is a varied set of diseases characterized by the presence of soft and hard drusen, altered pigmentation of the retinal pigment epithelium (RPE), RPE atrophy, and choroidal neovascularization (CNV). AMD is usually classified into two forms, namely dry and wet AMD. Dry AMD involves the accumulation of debris and deposits in the outer retina, along with atrophic and hypertrophic changes in the RPE, particularly underlying the central retina. Wet AMD is a pathological process, secondary to angiogenic neovascular changes (e.g., CNV) that occur in about 20% of patients with AMD. It remains unclear whether the two forms (wet and dry) are different manifestations of the same disorder, or distinct diseases with distinct origins and pathology. Recently, treatments for wet AMD have been developed. For example, antibodies against Vascular Endothelial Growth Factor (VEGF) such as AVASTIN® and LUCENTIS® from Genentech (South San Francisco, Calif.) have shown a benefit in treating established AMD in some cases.

In addition to AMD, other retinal disorders have been described. Retinitis pigmentosa (RP) is caused by mutations that compromise rod photoreceptor cells (rods) and lead to their death. Some mutations cause rapid death of rod cells, while others lead to a slow loss of these cells. Regardless of the mechanism, however, a common feature is the loss of the rod photoreceptors. As a result of this loss, patients become unable to see in dim illumination, but retain the ability to read and drive when lighting is sufficient. These remaining activities are mediated by cone photoreceptors, which remain intact until most of the rods have died and then they begin to die. Thus, prevention of both rod and cone photoreceptor cell death is desirable as a method of treating or preventing RP.

Glaucoma is another common blinding illness. It involves the loss of the output neurons of the retina, the ganglion cells. In many cases, this death is accompanied by increased intraocular pressure, while in other cases, the pressure is in the normal range. In all cases, ganglion cells die and blindness is the result.

A variety of mouse models are used to investigate retinal cell death and retinal disorders. In particular, because little rod cell death occurs during normal development, retinal cell survival is commonly investigated in a model of retinal degeneration. Mutations in the rod-specific gene phosphodiesterase 6β (PDE 6 β subunit) causes photoreceptor degeneration in several types of animals as well as humans. In mice, this mutation is also known as the rd1 mutation (Bowes et al. (1990) *Nature* 347:677; McLaughlin et al. (1993) *Nat. Genet.* 4:130-4; Rakoczy et al. (2006) *Exp. Eye Res.* 82(5):741, Epub Dec. 1, 2005). Rd1/rd1 mice are homozygous for a nonsense mutation in exon 7 of the Pde6β gene, which completely disrupts production of the β subunit of rod phosphodiesterase (Carter-Dawson et al., 1978). The rods develop, but then undergo rapid degeneration between postnatal day (P) 12 and P21. Thus, mice harboring the mutation are useful models of retinal cell disorders, particularly with respect to photoreceptor degeneration in rod cells. For example, rd1 mice are used as a model for retinitis pigmentosa (RP) in humans (Komeima et al. (2007) *J. Cell Physiol.* 213:809). Rd1 mice are also used as models for age-related macular degeneration (AMD). (Rohrer et al. (2007) *Exp. Eye Res.* 84(1):82, Epub Oct. 25, 2006).

The molecular events underlying blindness remain unclear. Because cell death is an important aspect of blindness, molecules and processes involved in regulating cell survival through control of DNA are under active investigation. A key cell survival mechanism is regulation of gene expression by lysine acetylation of histone proteins. Lysine acetylation is the transfer of an acetyl moiety from acetyl-coenzyme A (CoA) to the ε-amino group of a lysine residue. The acetylation is reversible and is controlled in vivo by the competing actions of acetyltransferases and deacetylases, which remove the acetyl moiety. Early research identified histone proteins as a major substrate for lysine acetylation and subsequent research identified many proteins as substrates for in histone acetylation or histone deacetylases (HDACs). Because histone proteins are involved in regulating gene expression, HDACs have been researched primarily as transcriptional corepressors that catalyze histone deacetylation (Nagy et al., 1997; Strahl and Allis, 2000).

Several classes of HDACs exist (see Yang and Grégoire (2005) *Mol. Cell. Biol.* 25:2873). The class IIA histone deacetylases, which include HDAC4, -5, -7 and -9, share several features. They bind MEF2 and repress its activity, and they undergo intracellular trafficking between the cytoplasm and nucleus. This trafficking is regulated by signal-induced phosphorylation (Miska et al. (1999) *Embo. J.* 18:5099). For example, HDAC4 can be phosphorylated by calcium/calmodulin-dependent kinase IV (CaMKIV) (Zhao et al. (2001) *J. Biol. Chem.* 276:35042). Phosphorylation recruits the phospho-binding protein 14-3-3, and the resulting complex is exported efficiently from the nucleus (Wang and Yang (2001) *Mol. Cell. Biol.* 21:5992). HDAC4 can subsequently reenter the nucleus after dephosphorylation and dissociation from 14-3-3 (Grozinger and Schreiber (2000) *Proc. Natl. Acad. Sci. USA* doi 10.1073).

There is a need in the art for therapies to prevent, treat, diagnose and prognose vision loss that results from decreased retinal cell function due to one or more retinal disorders or one or more natural events.

SUMMARY

The present invention is based in part on the discovery that HDAC4, HDAC5 and HDAC6 each plays an important role in neural (e.g., retinal) cell survival. HDAC7 has been found to have a similar distribution in retinal cells to those of HDACs 4, 5, and 6 and due to both its high degree of homology to the other Class IIa HDACs and its similar distribution, it is also involved in neural (e.g., retinal) cell survival. The present invention is further based in part on the discovery that HIF1α also plays an important role in neural (e.g., retinal) cell survival.

In certain exemplary embodiments, a method for inhibiting retinal cell death comprising expressing exogenous HDAC4 and/or exogenous HIF1α in one or more retinal cells in an amount sufficient to inhibit death of the retinal cells is provided. In certain aspects the retinal cells are, for example, bipolar cells, rod photoreceptor cells, cone photoreceptor cells, and combinations thereof. Retinal cell death can be naturally occurring or caused by a retinal disorder such as, for example, age-related macular degeneration or retinitis pigmentosa.

In certain aspects, a nucleic acid sequence encoding exogenous HDAC4 and/or exogenous HIF1α is delivered to the retinal cell by in vivo electroporation and/or by a viral vector. In certain aspects, exogenous HDAC4 is expressed in the cytoplasm. Exogenous HDAC4 can include a mutation that causes the exogenous HDAC4 to be localized in the cytoplasm of the neuronal cell such as, e.g., the phenotype observed for HDAC4-L175A. In certain aspects, exogenous HIF1α is not acetylated by ARD1, is not ubiquitinated and/or does not undergo proteasomal degradation. In certain aspects, exogenous HIF1α includes a mutation causing the exogenous HIF1α to be constitutively active.

In certain exemplary embodiments, a method of inhibiting retinal cell death comprising inhibiting degradation of endogenous HDAC4 in a retinal cell to inhibit death of the retinal cell is provided.

In certain exemplary embodiments, a method of inhibiting retinal cell death comprising preventing ARD1 from acetylating HIF1α in a retinal cell to inhibit death of the retinal cell is provided. In certain aspects, HIF1α ubiquitination is inhibited.

In certain exemplary embodiments, a method of inhibiting bipolar cell death comprising expressing exogenous HDAC6 in a bipolar cell in an amount sufficient to inhibit death of the bipolar cell is provided.

In another aspect, the present invention provides methods of inhibiting neuronal cell death. The methods include contacting the cell with an agent which enhances the expression and/or activity of HDAC4 or HIF1α, thereby inhibiting death of the retinal cell.

In yet another aspect, the present invention provides methods for treating or preventing a neurodegenerative disorder in a subject. The methods include administering to the subject an agent which enhances the expression and/or activity of HDAC4 or HIF1α, thereby treating or preventing said neurodegenerative disorder in the subject.

Cells suitable for use in the methods of the invention include a retinal cell, such as a bipolar cell, a rod photoreceptor cell or a cone photoreceptor cell.

Agents for use in the methods of the invention include nucleic acid molecules. Suitable nucleic acid molecule may be expressed in the cytoplasm of the cell. For example, in one embodiment, the nucleic acid molecule comprises an HDAC4 gene comprising a mutation that causes the exogenous HDAC4 to be localized to the cytoplasm of the cell, such as HDAC4-L175A. In other embodiments of the invention, the nucleic acid molecule comprises an HIF1α gene which is not acetylated by ARD1. In one embodiment, the nucleic acid molecule comprises an HIF1α gene which is not ubiquitinated. In yet another embodiment, the nucleic acid molecule comprises an HIF1α gene which is not degraded by the proteasome. In another embodiment, the nucleic acid molecule comprises an HIF1α gene comprising a mutation that causes the exogenous HIF1α to be constitutively active.

Neuronal cell death may be naturally occurring, caused by a neurodegenerative disorder, such as age-related macular degeneration or retinitis pigmentosa.

In other aspects, the present invention provides methods of inhibiting neuronal cell death. The methods include contacting the cell with an agent that inhibits degradation of HDAC4 in the cell or an agent that prevents ARD1 from acetylating HIF1α in said cell. In one embodiment, HIF1α ubiquitination is inhibited.

In another aspect, the invention provides methods of inhibiting bipolar cell death. The methods include contacting the cell with an agent that enhances the expression and/or activity of HDAC6 in said cell, thereby inhibiting death of said bipolar cell.

In one embodiment, the nucleic acid molecule is contained within a vector, for example, a retrovirus, an adenovirus, an adenoviral/retroviral chimera, an adeno-associated virus (AAV), a herpes simplex virus I or II, a parvovirus, a reticuloendotheliosis virus, a poliovirus, a papillomavirus, a vaccinia virus and a lentivirus. In a particular embodiment, the vector is an AAV vector, for example, an AAV 2/5 or an AAV 2/8 vector.

DETAILED DESCRIPTION

Figure 1:
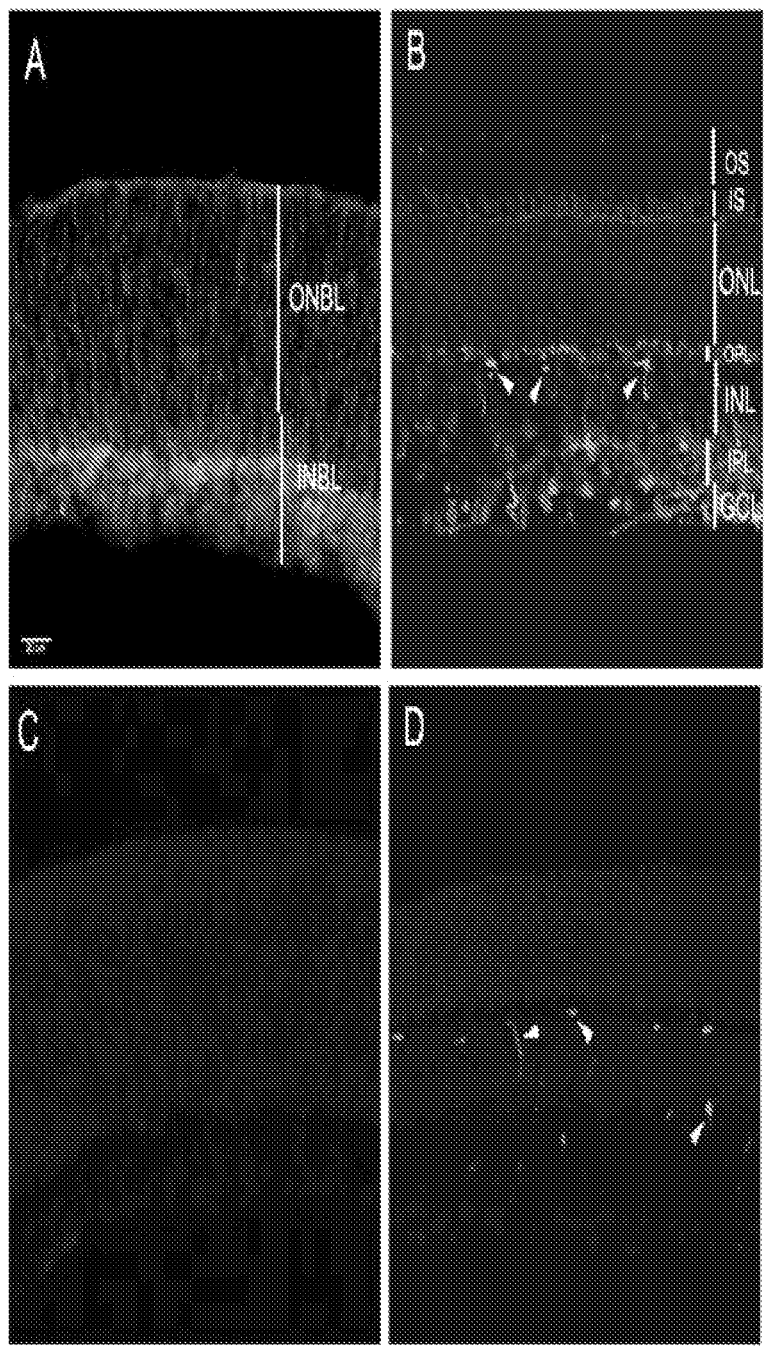
FIGS. 1A-1D illustrate HDAC4 expression in the developing and mature mouse retina. (A, B) HDAC4 immunohistochemistry on retinal sections at P1 and P21, respectively. (C, D) Pre-incubation of the anti-HDAC4 antibody with blocking peptide led to lack of staining at P1 and P21. Arrowheads (B, D), blood vessels labeled by the mouse antibody.

The present invention is based in part on the discovery that HDAC4, HDAC5 and HDAC6 each plays an important role in neural (e.g., retinal) cell survival. HDAC7 has been found to have a similar distribution in retinal cells to those of HDACs 4, 5, and 6 and due to both its high degree of homology to the other Class IIa HDACs and its similar distribution, it is also involved in neural (e.g., retinal) cell survival. The present invention is further based in part on the discovery that HIF1α also plays an important role in neural (e.g., retinal) cell survival. Accordingly, the present invention provides methods for inhibiting neuronal (e.g., retinal) cell death. Such methods generally comprise contacting a neuronal (e.g., retinal) cell with an agent, such as an HDAC4, HDAC6, HDAC7, or HDAC5 and/or HIF1α nucleic acid molecule, as described herein. The present invention also provides methods for treating a subject with a retinal neurodegenerative disorder. The methods generally comprise administering to a subject an effective amount of an agent, such as an HDAC4, HDAC6, HDAC7, or HDAC5 and/or HIF1α nucleic acid molecule, as described herein.

In certain embodiments of the invention, the nucleic acid molecule is contained within a vector, such as a retrovirus, an adenovirus, an adenoviral/retroviral chimera, an adeno-associated virus (AAV), a herpes simplex virus I or II, a parvovirus, a reticuloendotheliosis virus, a poliovirus, a papillomavirus, a vaccinia virus and a lentivirus. In one embodiment, the vector is an AAV vector. In one embodiment, the AAV vector is an AAV 2/5 or an AAV 2/8 vector. In other embodiments of the invention, the nucleic acid molecule is not contained within a vector.

The principles of the present invention may be applied with particular advantage to treat, prevent and/or delay neuronal (e.g., retinal) cell loss by increasing the levels of one or more proteins or portions of proteins expressed in a neuronal (e.g., retinal) cell.

In certain aspects, the levels of one or more HDAC proteins (e.g., HDAC4, HDAC5, HDAC7, HDAC9, and/or HDAC6) or portions thereof and/or HIF1α proteins or portions thereof are altered, i.e., increased, in an organism to treat, prevent and/or delay neuronal (e.g., retinal) cell loss.

The principles of the present invention may also be applied to promote and/or accelerate neuronal (e.g., retinal) cell loss by decreasing the levels of one or more proteins or portions of proteins expressed in a neuronal (e.g., retinal) cell. In certain aspects, the levels of one or more HDAC proteins (e.g., HDAC4, HDAC5, HDAC7, HDAC6, and/or HDAC9) or portions thereof and/or HIF1α proteins or portions thereof are altered, i.e., decreased in an organism to treat aberrant proliferation of neuronal (e.g., retinal) cells by promoting and/or accelerating neuronal (e.g., retinal) cell loss.

In one aspect of the invention, retinal cell survival is improved by expressing cytoplasmic mutants of HDAC4. In certain aspects, cytoplasmic mutants are HDAC4 mutants that are present in the cytoplasm to a greater extent, and in the nucleus to a lesser extent, than the wild-type protein. Several cytoplasmic mutants are known in the art; for example, HDAC4-L175A and HDAC4-Δ118 (Wang and Yang (2001) *Mol. Cell. Biol.* 21:5992). In certain aspects, it is desirable that the cytoplasmic HDAC4 mutant is predominately present in the cytoplasm with only minimal nuclear presence. The cytoplasmic HDAC4 mutant protein may not have any nuclear presence. Increased cytoplasmic HDAC4 may also be accomplished by the activation or overexpression of proteins known to promote increased residence of HDAC4 in the cytoplasm; for example, CaM kinases I, II, IV, 14-3-3 protein and the like (See Yang and Grégoire 25 (8): 2873. (2005) and references therein).

Increasing HIF1α protein levels prevents rod photoreceptor cell loss in rd1 mice. Accordingly, in certain aspects of the invention, an increased level of HIF1α in a neural cell is desired. Increased HIF1α levels may be achieved by stabilization of endogenously expressed protein, for example, by overexpression of HDAC4. In certain exemplary embodiments, increased HIF1α levels may be achieved by other methods such as overexpression of HIF1α protein. Overexpression may be achieved by any suitable method known in the art, including the methods described herein with respect to increasing the levels of HDAC4 protein. Increased levels of HIF1α are achieved when HIF1α protein is detected above endogenous levels. In other exemplary embodiments, a constitutively active HIF1α protein may be provided.

In yet another aspect, the inventors have provided a method of improving survival of bipolar (BP) cells by increasing the levels of HDAC4 and/or HDAC6. Delivery of nucleic acids to progenitors of BP cells can be accomplished, for example, by retroviral infection. By increasing expression levels of HDAC4 and/or HDAC6 in the progenitor cells, an increased number of bipolar cells is achieved. The increase in number of bipolar cells may be about 2-fold, 3-fold, 4-fold, 5-fold, 6-fold, 8-fold, 10-fold, 12-fold or greater.

In certain aspects, exogenous HDAC (e.g., HDAC4 and/or HDAC6) and/or exogenous HIF1α, and/or portions thereof are expressed in or contacted to neuronal (e.g., retinal) cells such that total HDAC (e.g., HDAC4 and/or HDAC6) or total HIF1α levels are increased in the cell after exogenous HDAC (e.g., HDAC4 and/or HDAC6) or exogenous HIF1α expression when compared to total HDAC (e.g., HDAC4 and/or HDAC6) or total HIF1α levels prior to exogenous HDAC or exogenous HIF1α expression. After exogenous expression of HDAC (e.g., HDAC4 and/or HDAC6) and/or HIF1α, total HDAC (e.g., HDAC4 and/or HDAC6) or total HIF1α levels can be increased by about 5%, 10%, 15%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000% or more over total HDAC (e.g., HDAC4 and/or HDAC6) or total HIF1α levels prior to exogenous HDAC (e.g., HDAC4 and/or HDAC6) or exogenous HIF1α expression.

In other aspects, neuronal (e.g., retinal) cells are contacted with an agent described herein that decreases HDAC (e.g., HDAC4 and/or HDAC6) or HIF1α levels in the cell when compared to total HDAC (e.g., HDAC4 and/or HDAC6) or total HIF1α levels prior to contact with the agent. After contact with the agent, HDAC (e.g., HDAC4 and/or HDAC6) or HIF1α levels can be decreased to about 5%, 10%, 15%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000% or more over total HDAC (e.g., HDAC4 and/or HDAC6) or total HIF1α levels prior to contact with the agent.

As used herein, the term "contacting" (i.e., contacting a cell with an agent) is intended to include incubating the agent and the cell together in vitro (e.g., adding the agent to cells in culture) or administering the agent to a subject such that the agent and cells of the subject are contacted in vivo. The term "contacting" is not intended to include exposure of cells to an agent that may occur naturally in a subject (i.e., exposure that may occur as a result of a natural physiological process).

In certain exemplary embodiments, the present invention provides methods and materials for treating, preventing and/or delaying disorders and diseases associated with neuronal cells in an organism such as, for example, neurodegenerative disorders.

As used herein, the term "neurodegenerative disorder" includes, but is not limited to, neurodegenerative disorders of the eye such as retinal disorders, e.g., atrophic macular degeneration, retinitis pigmentosa, iatrogenic retinopathy, retinal tears and holes, diabetic retinopathy, sickle cell retinopathy, retinal vein and artery occlusion and the like. Neurodegenerative disorders also include, but are not limited to, certain ophthalmic disorders, such as sickle cell retinopathy and retinal vein or artery occlusion, that can be characterized by both angiogenesis and neurodegenerative components. Neurodegenerative disorders further include disorders such as optic neuropathy, Alzheimer's disease, Parkinson's disease, Huntington's disease, Pick's disease, Pelizaeus-Merzbacher disease, Resfum's disease, Sandhoff disease, Schilder's disease, Steele-Richardson-Olszewski disease, amyotrophic lateral sclerosis, primary lateral sclerosis, multiple sclerosis, multiple system atrophy, narcolepsy, neuroborreliosis, spinocerebellar ataxia, spinal muscular atrophy, tabes dorsalis, prion diseases (e.g., scrapie, Creutzfeldt-Jakob disease, Gerstmann-Strassler Scheinker disease, bovine spongiform encephalopathy and the like), Alexander disease, Alper's disease, ataxia telangiectasia, Batten disease, Canavan disease, Cockayne syndrome, corticobasal degeneration, HIV-associated dementia, Kennedy's disease, Krabbe disease, Lewy body dementia, spinocerebellar ataxia type 3, subacute combined degeneration of spinal cord secondary to pernicious anemia, schizophrenia, Batten disease and the like.

In certain exemplary embodiments, the present invention provides methods and materials for promoting and/or accelerating cell loss (e.g., neuronal (e.g., retinal) cell loss) to treat, prevent and/or delay one or more disorders and/or diseases associated with aberrant neuronal cell proliferation, e.g., cancer.

Cellular proliferative disorders are intended to include disorders associated with rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal. Id. Such abnormal tissue shows partial or complete lack of structural organization and functional coordination with the normal tissue which may be either benign (i.e., benign tumor) or malignant (i.e., malignant tumor).

Examples of the types of neoplasms intended to be encompassed by the present invention include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys.

As used herein, the term "organism" includes, but is not limited to, a human, a non-human primate, a cow, a horse, a sheep, a goat, a pig, a dog, a cat, a rabbit, a mouse, a rat, a gerbil, a frog, a toad and a transgenic species thereof. The term "organism" further includes, but is not limited to, a yeast cell, a yeast tetrad, a yeast colony, a bacterium, a bacterial colony, a virion, virosome, virus-like particle and/or cultures thereof, and the like.

In one embodiment of the invention, cells suitable for use in the instant methods are neuronal cells. As used herein, the terms "neuron" or "neuronal cell" refer to a nerve cell capable of receiving and conducting electrical impulses from the nervous system. A nerve cell or "neuron" typically comprises a cell body, an axon, axon terminals, and dendrites and is readily identifiable by one of ordinary skill in the art.

In one embodiment, a neuron is a "photoreceptor cell", i.e., a specialized neuron found in the retina. The retina is a thin, transparent tissue containing about 120 million separate rod cells (night vision) and 7 million cone cells (day and color vision) as well as millions of other structural supporting and interconnecting cells. Photoreceptor cells consist of "rods" and "cones", which are the photosensitive cells of the retina. The rods contain rhodopsin, the rod photopigment, and the cones contain other distinct photopigments, which respond to light and ultimately trigger a neural discharge in the output cells of the retina, the ganglion cells. Ultimately, this signal is registered as a visual stimulus in the visual cortex and other target locations in the brain. The retinal pigment epithelial (RPE) cells produce, store and transport a variety of factors that are responsible for the normal function and survival of photoreceptors. Retinal neurons that can also sense light consist of photosensitive ganglion cells. These cells, known as the melanopsin ganglion cells are found in the inner retina, have dendrites and long axons projecting to the protectum (midbrain), the suprachiasmatic nucleas in the hypothalamus, and the lateral geniculate (thalamus). The retina also consists of bipolar cells which exist between photoreceptors (rod cells and cone cells) and ganglion cells. These cells transmit signals from the photoreceptors to the ganglion cells. Bipolar cells receive synaptic input from either rods or cones, but not both, and they are designated rod bipolar or cone bipolar cells respectively. In one embodiment, a photoreceptor cell is a rod. In one embodiment, a photoreceptor cell is a cone. In one embodiment, a photosensitive cell is a cell is a bipolar cell.

Certain aspects of the invention pertain to vectors, such as, for example, expression vectors, containing a nucleic acid encoding one or more HDAC and/or HIF1α proteins (and/or portion(s) thereof). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." LTRs contain numerous regulatory signals, including transcriptional control elements, polyadenylation signals, and sequences needed for replication and integration of the viral genome. LTRs may be several hundred base pairs in length.

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) *Curr. Topics Microbiol. Immunol.* 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) *J. Virology* 76(5):2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

As used herein, the term "adenovirus" ("Ad") refers to a group of double-stranded DNA viruses with a linear genome of about 36 kb. See, e.g., Berkner et al., Curr. Top. Microbiol. Immunol., 158: 39-61 (1992). In some embodiments, the adenovirus-based vector is an Ad-2 or Ad-5 based vector. See, e.g., Muzyczka, Curr. Top. Microbiol. Immunol., 158: 97-123, 1992; Ali et al., 1994 Gene Therapy 1: 367-384; U.S. Pat. Nos. 4,797,368, and 5,399,346. Suitable adenovirus vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types. Additionally, introduced adenovirus DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenovirus genome for foreign DNA is large (up to 8 kilobases) relative to other gene delivery vectors (Haj-Ahmand et al. J. Virol. 57, 267-273 [1986]).

In one embodiment, an adenovirus is a replication defective adenovirus. Most replication-defective adenoviral vectors currently in use have all or parts of the viral E1 and E3 genes deleted but retain as much as 80% of the adenovirus genetic material. Adenovirus vectors deleted for all viral coding regions are also described by Kochanek et al. and Chamberlain et al. (U.S. Pat. No. 5,985,846 and U.S. Pat. No. 6,083,750). Such viruses are unable to replicate as viruses in the absence of viral products provided by a second virus, referred to as a "helper" virus.

In one embodiment, an adenoviral vector is a "gutless" vector. Such vectors contain a minimal amount of adenovirus DNA and are incapable of expressing any adenovirus antigens (hence the term "gutless"). The gutless replication defective Ad vectors provide the significant advantage of accommodating large inserts of foreign DNA while completely eliminating the problem of expressing adenoviral genes that result in an immunological response to viral proteins when a gutless replication defective Ad vector is used in gene therapy. Methods for producing gutless replication defective Ad vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

In another embodiment, an adenoviral vector is a "conditionally replicative adenovirus" ("CRAds"). CRAds are genetically modified to preferentially replicate in specific cells by either (i) replacing viral promoters with tissue specific promoters or (ii) deletion of viral genes important for replication that are compensated for by the target cells only. The skilled artisan would be able to identify epithelial cell specific promoters.

Other art known adenoviral vectors may be used in the methods of the invention. Examples include Ad vectors with recombinant fiber proteins for modified tropism (as described in, e.g., van Beusechem et al., 2000 Gene Ther. 7: 1940-1946), protease pre-treated viral vectors (as described in, e.g., Kuriyama et al., 2000 Hum. Gene Ther. 11: 2219-2230), E2a temperature sensitive mutant Ad vectors (as described in, e.g., Engelhardt et al., 1994 Hum. Gene Ther. 5: 1217-1229), and "gutless" Ad vectors (as described in, e.g., Armentano et al., 1997 J. Virol. 71: 2408-2416; Chen et al., 1997 Proc. Nat. Acad. Sci. USA 94: 1645-1650; Schieder et al., 1998 Nature Genetics 18: 180-183).

The recombinant expression vectors of the invention comprise a nucleic acid of the invention (e.g., a nucleic acid sequence encoding one or more HDAC and/or HIF1α proteins and/or portion(s) thereof) in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or portions thereof, including fusion proteins or portions thereof, encoded by nucleic acids as described herein (e.g., one or more HDAC and/or HIF1α proteins and/or portion(s) thereof).

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleic acid molecule used in the methods of the present invention can be isolated using standard molecular biology techniques. Using all or portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques. Furthermore, oligonucleotides corresponding to nucleotide sequences of interest can be prepared by standard synthetic techniques, e.g., using an automated DNA synthesizer.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In one embodiment of the invention, an agent for use in the methods of the invention is a nucleic acid molecule encoding a protein of interest. For example, a cDNA (full length or partial cDNA sequence) is cloned into a recombinant expression vector and the vector is transfected into cells using standard molecular biology techniques. The cDNA can be obtained, for example, by amplification using the polymerase chain reaction (PCR) or by screening an appropriate cDNA library.

Following isolation or amplification of a cDNA, the DNA fragment is introduced into a suitable expression vector. For example, nucleic acid molecules encoding a protein of interest in the form suitable for expression of the protein in a host cell, can be prepared using nucleotide sequences based on the nucleic acid sequence of a nucleic acid molecule encoding the protein of interest.

In one embodiment, a nucleic acid molecule can be present in an inducible construct. In another embodiment, a nucleic acid molecule can be present in a construct which leads to constitutive expression.

In one embodiment, the nucleic acid molecules of the invention may be delivered to cells, e.g., neuronal cells, or to subjects, in the absence of a vector. In certain embodiments, the nucleic acid molecules of the invention may be delivered to cells, e.g., neuronal cells, or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107 (Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401 (1996); and Kramm, C. M., et al., Brain Pathology 5:345-381 (1995). Such vectors may be derived from viruses that contain RNA (Vile, R. G., et al., Br. Med. Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283).

In a particular embodiment, the viral vector for use in the methods of the present invention is an AAV vector. In particular embodiments, the viral vector is an AAV2/5 or AAV2/8 vector. Such vectors are described in, for example, U.S. Pat. No. 7,056,502, the entire contents of which are incorporated herein by reference.

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected animals for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. The virus can be placed in contact with the neuronal cell of interest or alternatively, can be injected into a subject suffering from a neurodegenerative disorder.

Delivery of nucleic acids described herein (e.g., vector DNA) can be by any suitable method in the art. For example, delivery may be by injection (e.g., intravitreal or subretinal injection), gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEIT™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470), stereotactic injection (see, e.g., Chen et al. (1994) *Proc. Natl. Acad. Sci. U.S.A.* 91:3054) or by in vivo electroporation (see, e.g., Matsuda and Cepko (2007) *Proc. Natl. Acad. Sci. U.S.A.* 104:1027). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Any suitable virus usable for nucleic acid delivery may be used, including, but not limited to, adenovirus, adeno-associated virus, retroviruses and the like. For example, the LIA retrovirus may be used to deliver nucleic acids (Cepko et al. (1998) *Curr. Top. Dev. Biol.* 36:51; Dyer and Cepko (2001) *J. Neurosci.* 21:4259). The viral titer may be varied to alter the expression levels. The viral titer may be in any suitable range. For example, the viral titer can have an upper limit of about $10^5$ cfu/ml, $10^6$ cfu/m, $10^7$ cfu/ml, $10^8$ cfu/ml, $10^9$ cfu/ml, $10^{10}$ cfu/ml, $10^{11}$ cfu/ml or more. The viral titer can have a lower limit of about $10^{13}$ cfu/ml $10^{12}$ cfu/ml, $10^{11}$ cfu/ml, $10^{10}$ cfu/ml, $10^9$ cfu/ml, $10^8$ cfu/ml, $10^7$ cfu/ml, $10^6$ cfu/ml or less. Often, the viral titer ranges from about $10^6$ cfu/ml to $10^8$ cfu/ml. More often, the range is about $10^7$ cfu/ml to $10^8$ cfu/ml. The amount of virus to be added may also be varied. The volume of virus, or other nucleic acid and reagent, added can be in any suitable range. For example the volume may have an upper limit of about 100 µl, 200 µl, 300 µl, 400 µl, 500 µl, 750 µl, 1000 µl, 1250 µl, 1500 µl or more. The volume may have a lower limit of about 1250 µl, 1000 µl, 750 µl, 500 µl, 400 µl, 300 µl, 200 µl, 100 µl, 50 µl, 25 µl or less.

Recombinant expression vectors of the invention can be designed for expression of one or more HDAC and/or HIF1α proteins and/or portion(s) thereof in prokaryotic or eukaryotic cells. For example, one or more HDAC and/or HIF1α proteins and/or portion(s) thereof can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40); pMAL (New England Biolabs, Beverly, Mass.); and pRIT5 (Pharmacia, Piscataway, N.J.) which fuse glutathione S-transferase (GST), maltose E binding protein, or protein A, respectively, to the target recombinant protein.

In another embodiment, the HDAC and/or HIF1α proteins and/or portion(s) thereof expression vector is a yeast expression vector. Examples of vectors for expression in yeast *S. cerevisiae* include pYepSec1 (Baldari, et. al., (1987) *EMBO J.* 6:229-234); pMFa (Kurjan and Herskowitz, (1982) *Cell* 30:933-943); pJRY88 (Schultz et al., (1987) *Gene* 54:113-123); pYES2 (Invitrogen Corporation, San Diego, Calif.); and picZ (Invitrogen Corporation).

Alternatively, HDAC and/or HIF1α proteins and/or portion(s) thereof can be expressed in insect cells using baculovirus expression vectors. Baculovirus vectors available for expression of proteins in cultured insect cells (e.g., Sf9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements.

For example, commonly used promoters are derived from polyoma, adenovirus 2, cytomegalovirus and simian virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include retinal cell-type-specific promoters (e.g., rhodopsin regulatory sequences, Cabp5, Cra1bp, Nr1, Crx, Ndrg4, clusterin, Rax, Hes1 and the like (Matsuda and Cepko, supra)), the albumin promoter (liver-specific, Pinkert et al. (1987) *Genes Dev.* 1:268), lymphoid-specific promoters (Calame and Eaton (1988) *Adv. Immunol.* 43:235), in particular promoters of T cell receptors (Winoto and Baltimore (1989) *EMBO J.* 8:729) and immunoglobulins (Banerji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. U.S.A.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374) and the α-fetoprotein promoter (Campes and Tilghman (1989) *Genes Dev.* 3:537).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more HDAC and/or HIF1α proteins and/or portion(s) thereof can be expressed in bacterial cells such as *E. coli*, viral cells such as retroviral cells, insect cells, yeast or mammalian cells (such as Chinese hamster ovary cells (CHO) or COS cells). Other suitable host cells are known to those skilled in the art.

Screening assays for identifying modulators, i.e., candidate or test compounds or agents (e.g., peptides, cyclic peptides, peptidomimetics, small molecules, small organic molecules, or other drugs) which have a stimulatory or inhibitory effect on one or more of the proteins or portions thereof described herein (e.g., one or more HDAC and/or HIF1α proteins and/or portion(s) thereof) are also provided.

As used herein, the term "small organic molecule" refers to an organic molecule, either naturally occurring or synthetic, that has a molecular weight of more than about 25 daltons and less than about 3000 daltons, usually less than about 2500 daltons, more usually less than about 2000 daltons, usually between about 100 to about 1000 daltons, more usually between about 200 to about 500 daltons.

In one embodiment, the invention provides assays for screening candidate or test compounds which are substrates of one or more of one or more HDAC and/or HIF1α proteins and/or portion(s) thereof described herein. In another embodiment, the invention provides assays for screening candidate or test compounds which bind to or modulate the activity of one or more HDAC and/or HIF1α proteins and/or portion(s) thereof described herein.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

The test compound(s), the one or more HDAC and/or HIF1α proteins and/or portion(s) thereof and/or nucleic acid sequences encoding one or more HDAC and/or HIF1α proteins and/or portion(s) thereof described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect of the invention, a therapeutic nucleic acid molecule or the vector containing the same will be in the form of a pharmaceutical composition containing a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for intraocular, parenteral, intravenous, intraperitoneal, topical, or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the gene therapy vector, use thereof in the pharmaceutical compositions of the invention is contemplated. Supplementary active compounds can also be incorporated into the compositions.

In a particular embodiment, the pharmaceutical compositions of the present invention would be administered in the form of injectable compositions. The vector can be prepared as an injectable, either as liquid solutions or suspensions. The preparation may also be emulsified. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In a particular embodiment, the nucleic acid molecules and/or vectors are incorporated in a composition suitable for intraocular administration. For example, the compositions may be designed for intravitreal, subconjuctival, sub-tenon, periocular, retrobulbar, suprachoroidal, and/or intrascleral administration, for example, by injection, to effectively treat the retinal disorder. Additionally, a sutured or refillable dome can be placed over the administration site to prevent or to reduce "wash out", leaching and/or diffusion of the active agent in a non-preferred direction.

Relatively high viscosity compositions, as described herein, may be used to provide effective, and preferably substantially long-lasting delivery of the nucleic acid molecules and/or vectors, for example, by injection to the posterior segment of the eye. A viscosity inducing agent can serve to maintain the nucleic acid molecules and/or vectors in a desirable suspension form, thereby preventing deposition of the composition in the bottom surface of the eye. Such compositions can be prepared as described in U.S. Pat. No. 5,292,724, the entire contents of which are hereby incorporated herein by reference.

Sterile injectable solutions can be prepared by incorporating the test compound(s), the one or more HDAC and/or HIF1α proteins and/or portion(s) thereof and/or nucleic acid sequences encoding one or more HDAC and/or HIF1α proteins and/or portion(s) thereof described herein in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the test compound(s), the one or more HDAC and/or HIF1α proteins and/or portion(s) thereof and/or nucleic acid sequences encoding one or more HDAC and/or HIF1α proteins and/or portion(s) thereof described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The test compound(s), the one or more HDAC and/or HIF1α proteins and/or portion(s) thereof and/or nucleic acid sequences encoding one or more HDAC and/or HIF1α proteins and/or portion(s) thereof described herein can also be prepared in the form of suppositories (e.g., with conventional suppository bases such as cocoa butter and other glycerides) or retention enemas for rectal delivery.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of the test compound(s), the one or more HDAC and/or HIF1α proteins and/or portion(s) thereof and/or nucleic acid sequences encoding one or more HDAC and/or HIF1α proteins and/or portion(s) thereof described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

One embodiment of the present invention involves a method for treatment of a neurodegenerative disorder, e.g., a neurodegenerative retinal disorder, which includes the step of administering a therapeutically effective amount of an agent, e.g., one or more test compounds, one or more HDAC and/or HIF1α proteins and/or mutants and/or portion(s) thereof or a nucleic acid sequence that encodes one or more HDAC and/or HIF1α proteins and/or mutants and/or portion(s) thereof, to a subject.

In certain aspects of the invention, the neurodegenerative disorder of the eye is associated with decreased viability of cone cells. In other aspects of the invention, the neurodegenerative disorder of the eye is associated with decreased viability of rod cells. In still other aspects, the neurodegenerative disorder of the eye is a genetic disorder.

As used herein, the term "administering" to a subject includes dispensing, delivering or applying a composition to a subject by any suitable route for delivery of the composition to the desired location in the subject, including delivery by intraocular (subretinal or subvitreal) administration or intravenous administration. Alternatively or in combination, delivery is by the topical, parenteral or oral route, intracerebral injection, intramuscular injection, subcutaneous/intradermal injection, intravenous injection, buccal administration, transdermal delivery and administration by the rectal, colonic, vaginal, intranasal or respiratory tract route.

In general, the agent, e.g., a nucleic acid molecule, is provided in a therapeutically effective amount to elicit the desired effect, e.g., inhibit neuronal cell death. The quantity of the vector to be administered, both according to number of treatments and amount, will also depend on factors such as the clinical status, age, and weight of the subject to be treated, and the severity of the disorder. Precise amounts of active ingredient required to be administered depend on the judgment of the gene therapist and will be particular to each individual patient. Generally, the viral vector is administered in titers ranging from about $1 \times 10^5$ to about $1 \times 10^9$ colony forming units (cfu) per ml, although ranges may vary. Preferred titers will range from about $1 \times 10^6$ to about $1 \times 10^8$ cfu/ml.

A therapeutically effective amount of an agent (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an agent can include a single treatment or, preferably, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

In one embodiment, a packaging cell line is transduced with a retroviral vector carrying the desired nucleic acid molecule to form a producer cell line. The packaging cells may be transduced by any means known in the art, including, e.g., electroporation, CaPO4 precipitation, or the use of liposomes. Examples of packaging cells that may be transfected include, but are not limited to, BOSC23, Bing, PE501, PA317, .PSI.-2, .PSI.-AM, PA12, T19-14X, VT-19-17-H2, .PSI.-CRE, .PSI.-CRIP, GP+E86, GP+envAm12, and DAN cell lines. Guidance on retroviral producing packaging cells and how to construct them can be found in Short et al., J. Neurosci. Res. 27:427-433 (1990); Miller, A. D., Human Gene Ther. 1:5-14 (1990); Danos, 0, "Construction of Retroviral Packaging Cell Lines," in Methods in Molecular Biology (M. Collins, ed.), Vol. 8, The Humana Press Inc., Clifton, N.J., 17-26 (1991); Murdoch, B., et al., Gene Therapy 4:744-749 (1997); and U.S. Pat. Nos. 5,529,774 and 5,591,624, the entire contents of which are incorporated herein by reference.

Retroviral vectors have also been successfully packaged with a vesicular stomatitis virus (VSV) envelope glycoprotein G ("pseudotyping"). These vectors are more stable and can be concentrated to $10^9$ cfu/ml, allowing them to be injected directly (Burns, J. C. et al. (1993) *Proc. Natl. Acad. Sci. USA* 90:8033-8037).

The producer cells can then be grafted near or into the desired location, for example, intraocularly. Direct injection of high titer retroviral producer cells (Murdoch, B., et al., Gene Ther. 4:744-749 (1997); Onodera, M., et al., Hum Gene Ther. 8:1189-1194 (1997)) should allow for efficient in situ infection with the retroviral sequences (Rainov, N. G., et al., Cancer Gene Ther. 3:99-106 (1996); Ram, Z., et al., Cancer Res. 53:83-88 (1993)). Producer cells injected intraocularly do not generally migrate from the site of injection. Moreover, although they may be rejected by the host, this does not occur for 5-10 days, by which time retroviral infection of nearby cells will have occurred (Ram, Z., et al., J. Neurosurg. 79:400-407 (1993)). In general, vector producer cell (VPC) dosages range from about $2.5 \times 10^8$ VPCs to about $1 \times 10^9$ VPCs. The exact amount of producer cells will ultimately be determined by the skilled artisan based on numerous factors, including, but not limited to, the available injectable volume, clinical status of the patient, and the severity of the disorder.

Preferably, the viral genomes of the viral vectors used in the invention should be modified to remove or limit their ability to replicate, however, replication conditional viruses will also be useful in the present invention, as will replicating vectors that are capable of targeting certain cells. (See, e.g., Zhang, J. et al. (1996) *Cancer Metastasis Rev.* 15:385-401).

In one embodiment, a single viral vector is used to carry multiple nucleic acid molecules, for example, genes encoding HDAC4 and HDAC6. In another embodiment, two viral vectors are used each carrying one or more genes of interest. If two viral vectors are used, they can be derived from the same or a different type of virus, and can be administered simultaneously or sequentially (i.e., without regard for a specific order).

The nucleic acid molecules can also be delivered using non-viral methods for gene transfer, preferably those whose use in gene therapy is known in the art (Nakanishi, M., Crit. Rev. Therapeu. Drug Carrier Systems 12:263-310 (1995); Abdallah, B., et al., Biol Cell 85:1-7 (1995); Zhang, J., et al., Cancer Metastasis Rev. 15:385-401 (1996); Philips, S.C., Biologicals 23:13-16 (1995); Lee, R. J. and Huang, L., Crit. Rev. Ther. Drug Carrier Syst. 14:173-206 (1997)). Examples of such non-viral vectors for gene delivery include prokaryotic vectors, cationic liposomes, DNA-protein complexes, non-viral T7 autogene vectors (Chen, X., et al., Hum. Gene Ther. 9:729-736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburstpolyamidoamine dendrimers (Kukowska-Latallo, J. F., et al., Proc Natl Acad Sci USA 93:4897-4902 (1996); Tang, M. X., et al., Bioconjug. Chem. 7:703-714 (1996)), cationic peptides (Wyman, T. B., et al., Biochemistry 36:3008-3017 (1997)), and mammalian artificial chromosomes (Ascenzioni, F., et al., Cancer Lett. 118:135-142 (1997)).

In addition, the present invention provides an embodiment of the foregoing methods wherein the nucleic acid molecules are delivered using any cellular vector, preferably one whose use for gene therapy is well-established for those skilled in the art. Examples of such cellular vectors for gene therapy include endothelial cells (Rancourt, C., et al., Clin. Cancer Res. 4:265-270 (1998); Qjeifo, J. O., et al., Cytokines Mol. Ther. 2:89-101 (1996)) and macrophages including tumor-infiltrating macrophages (Zufferey, R., et al., Nat. Biotechnol. 15:871-875 (1997); Naldini, L., et al., Science 272:263-267 (1996)), each of which may be modified using viral or non-viral vectors to carry the desired nucleic acid molecules, and thus express the desired gene products. Other suitable non-viral vectors will be readily apparent to the skilled artisan.

Gene delivery can be enhanced by including an internal ribosome entry site (IRES) sequence to achieve coordinate expression of multiple genes on a bicistronic message. IRESs are sequences containing 500-600 bp that are typical of the 5' nontransduced regions of picornaviruses, including the polio- and encephalomyocarditis viruses (EMCV). See, e.g., Ghattas, I. R., et al., Molecular and Cellular Biology 11:5848-5859 (1991); Morgan, R. A., et al., Nucleic Acids Research 20:1293-1299 (1992). This approach has been used for efficient retroviral coexpression of the two subunits of interleukin-12 (Tahara, H., et al., J. Immunol. 154:6466-6474 (1995)). Another alternative is for the vector to contain multiple genes under the control of distinct promoters.

In one embodiment of the invention, an agent as described herein is administered to a subject having a neurodegenerative retinal disorder or at risk of developing a neurodegenerative retinal disorder (e.g., a subject in which there is a family history of the neurodegenerative retinal disorder) prior to the onset of symptoms, such as loss of night-time vision due to, e.g., loss of rods. In another embodiment of the invention, an agent as described herein is administered to a subject having a neurodegenerative retinal disorder or at risk of developing a neurodegenerative retinal disorder (e.g., a subject in which there is a family history of the neurodegenerative retinal disorder) after the onset of symptoms, such as loss of night-time vision due to, e.g., loss of rods. In one embodiment, the cones of such a subject are viable.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, and accompanying claims.

EXAMPLES

The following materials and methods were used in Examples I-V.

Animals.

Wild-type CD1 and retinal degeneration rd1 (FVB stain) mice were purchased from the Charles River Laboratory.

HDAC4 RNAi and In Vivo Electroporation.

HDAC4 RNAi target sequence GGAGATGCTGGCCAT-GAAGCA (SEQ ID NO:1) was cloned into pBS/U6 RNAi construct ((Matsuda and Cepko (2004) Proc. Natl. Acad. Sci. USA 101:16). To produce the HDAC4 RNAi resistant expression vector, the shRNA target sequence was mutated (mutated nucleotides in small letters) to GGAaATGCTaGCtAT-GAAaCA (SEQ ID NO:2) using degenerate codons. pCAG-HDAC4, pCAG-HDAC6, and pCAG-dnHIF1α constructs were used for in vivo electroporations. Protocols for the screen to find an effective shRNA were described previously. Id.

TUNEL Assay, Immunohistochemistry and Fluorescence Microscopy.

TUNEL assay and immunohistochemistry were performed as previously described (Chen and Cepko (2007) BMC Dev. Biol. 7:78) (24). Fluorescence images of retinal sections were processed using the LEICA TCS SP2 confocal microscope. Fluorescence images of flat-mount retinas processed using Nikon ECLIPSE E1000 microscope. Primary antibody used: HDAC4 (Sigma, 1:200), blocking peptide for HDAC4 MSSQSHPDGLSGRDQPVEL (SEQ ID NO:3) was used at 0.1 µg/µl; Rho4D2 for rhodopsin ((Molday and MacKenzie (1983) Biochemistry 22:653) (25) 1:100); activated caspase-3 (Cell Signaling, 1:200); HIF1α (R&D Systems, 1:300).

Clonal Analysis.

Clonal analysis using replication-incompetent retrovirus LIA was performed as previously described (Cepko et al. (1998) Curr. Top. Dev. Biol. 36:51; Dyer, and Cepko (2001) J. Neurosci. 21:4259). LIA retrovirus was made as described and had a titer of approximately $1 \times 10^7$ cfu/ml. Half a microliter viral suspension was injected into the subretinal space of the P0 mouse retina. Retinas were fixed at P21 and AP stained for cells generated from viral-infected retinal progenitors.

Example I

HDAC Overexpression

Figure 9:
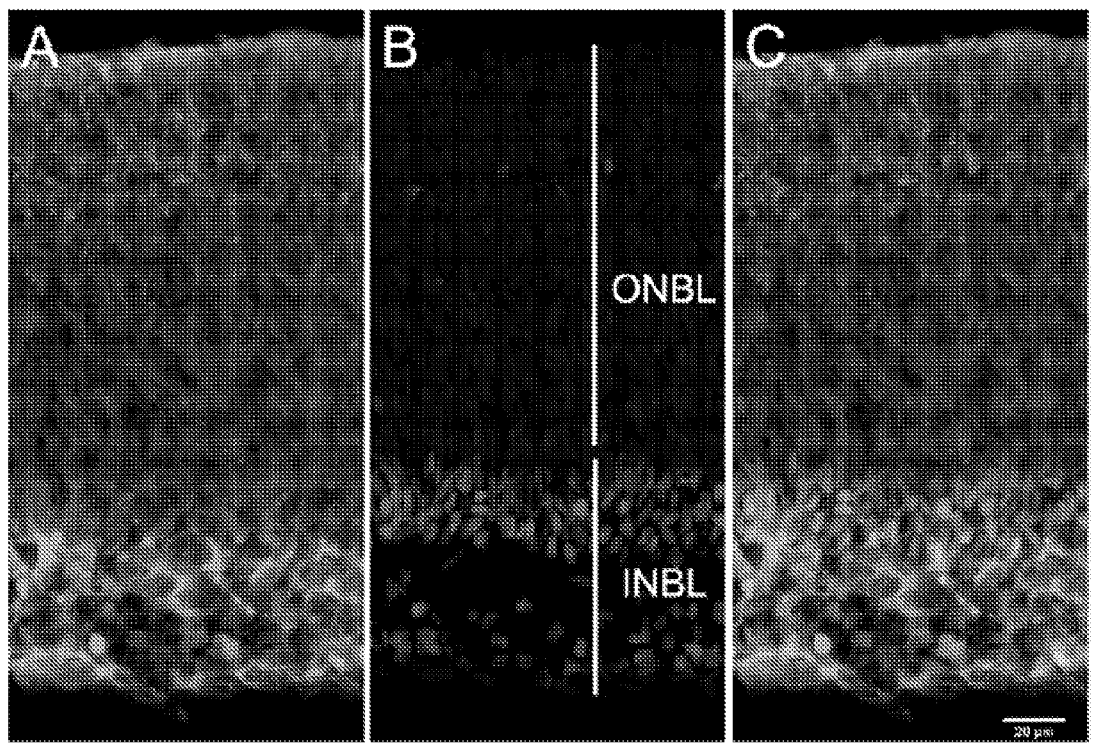
FIG. 9A-9C depict that HDAC4 is primarily cytoplasmic in the developing mouse retina. P1 retinal sections were double-immunostained for HDAC4 (A) and Pax6 (B), overlay in (C).

To examine HDAC4 expression in the mammalian retina, immunohistochemistry was performed using a monoclonal antibody. HDAC4 immunoreactivity was detected in the P1 retina (FIG. 1A) with strong signal in the inner neuroblastic layer (INBL). In the INBL, it was mostly excluded from the nuclei of developing amacrine cells (AC) and ganglion cells, as shown by co-immunostaining with an antibody for Pax6, a nuclear protein (FIG. 9). A cytoplasmic expression pattern of HDAC4 was observed across the ONBL, consisting of mitotic progenitor cells and newborn photoreceptor cells. HDAC4 immunoreactivity was lower in the mature retina (FIG. 1B). It was detected in the inner segment (IS) of photoreceptor cells, but not in the outer segments (OS), or in cell bodies located in the outer nuclear layer (ONL). In the inner nuclear layer (INL), faint immunoreactivity was detected in the cytoplasm of BP cells and AC. Nuclear staining was seen in the ganglion cell layer (GCL), and in the two plexiform layers where processes are located. HDAC4 immunoreactivity was specific as it was abolished by preincubation of the antibody with the cognate blocking peptide (FIGS. 1C, 1D).

Figure 2:
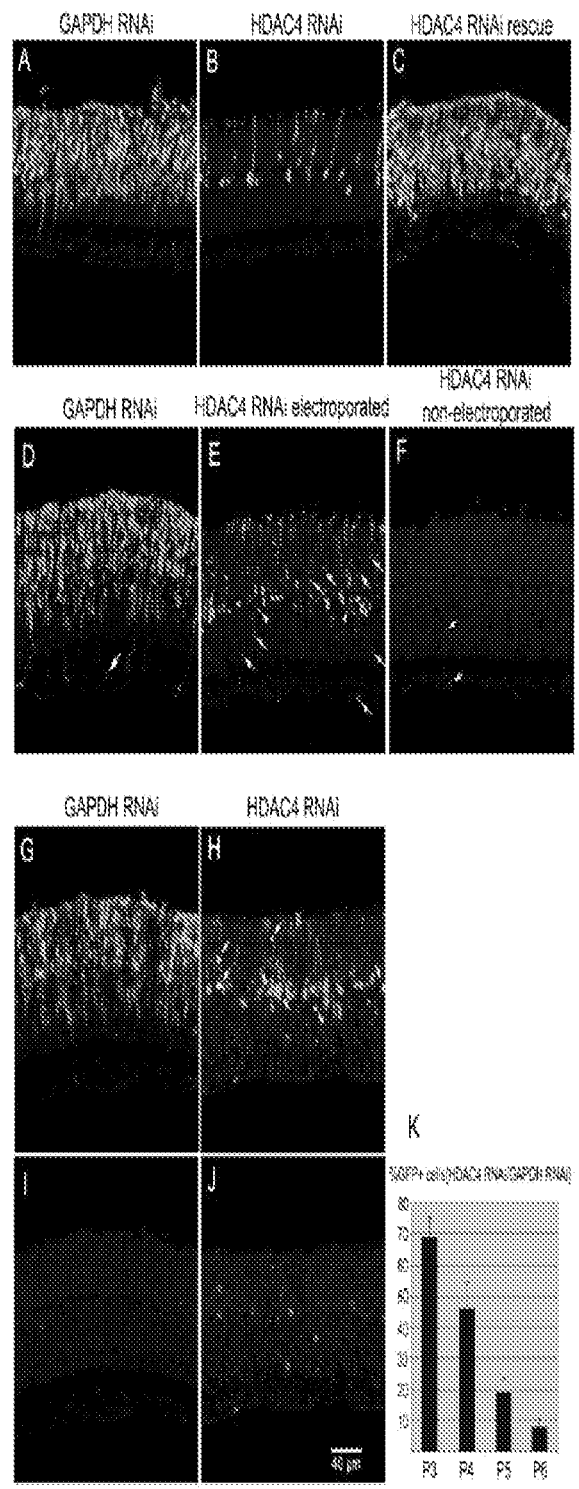
FIGS. 2A-2K illustrate that HDAC4 is essential for retinal cell survival. GAPDH (glyceraldehyde 3-phosphate dehydrogenase) or HDAC4 protein levels were decreased using RNAi, which was introduced by in vivo electroporation into the wild-type mouse retina at P0, with assay at P6 (A-C) or P5 (D-J). (A) Cryosections from retinas with GAPDH RNAi. (B) Cryosections from retinas with HDAC4 RNAi. (C) Cryosections from retinas with HDAC4 shRNA and an RNAi resistant HDAC4-expressing construct. (D-F) Terminal uridine deoxynucleotidyl transferase dUTP nick end labeling (TUNEL) analysis was used to detect apoptotic cell death. (D) Cryosections from retinas with GAPDH RNAi. Arrows indicate TUNEL+ cells. (E) Cryosections from retinas with HDAC4 RNAi. Arrows indicate TUNEL+ GFP− cells. Arrowheads indicate TUNEL+ GFP+ cells. (F) Cryosections from retinas with HDAC4 RNAi, from the non-electroporated area. Arrows indicate TUNEL positive cells. (G-J) Activated caspase-3 immunohistochemistry. (G) GAPDH RNAi retinal sections. (H) HDAC4 RNAi sections. Arrows indicate activated caspase-3+ GFP+ cells. (I) Image in (G) without GFP overlay. (J) Image in (H) without GFP overlay. (K) The number of GFP+ cells following electroporation of HDAC4 shRNA or GAPDH shRNA was counted per 100 μm section from three electroporated retinas for each treatment at P3, P4, P5 and P6. the number of GFP+ cells observed in retinas with HDAC4 shRNA was expressed as a percentage of the number of GFP+ cells in cells electroporated by GAPDH shRNA.
Figure 6:
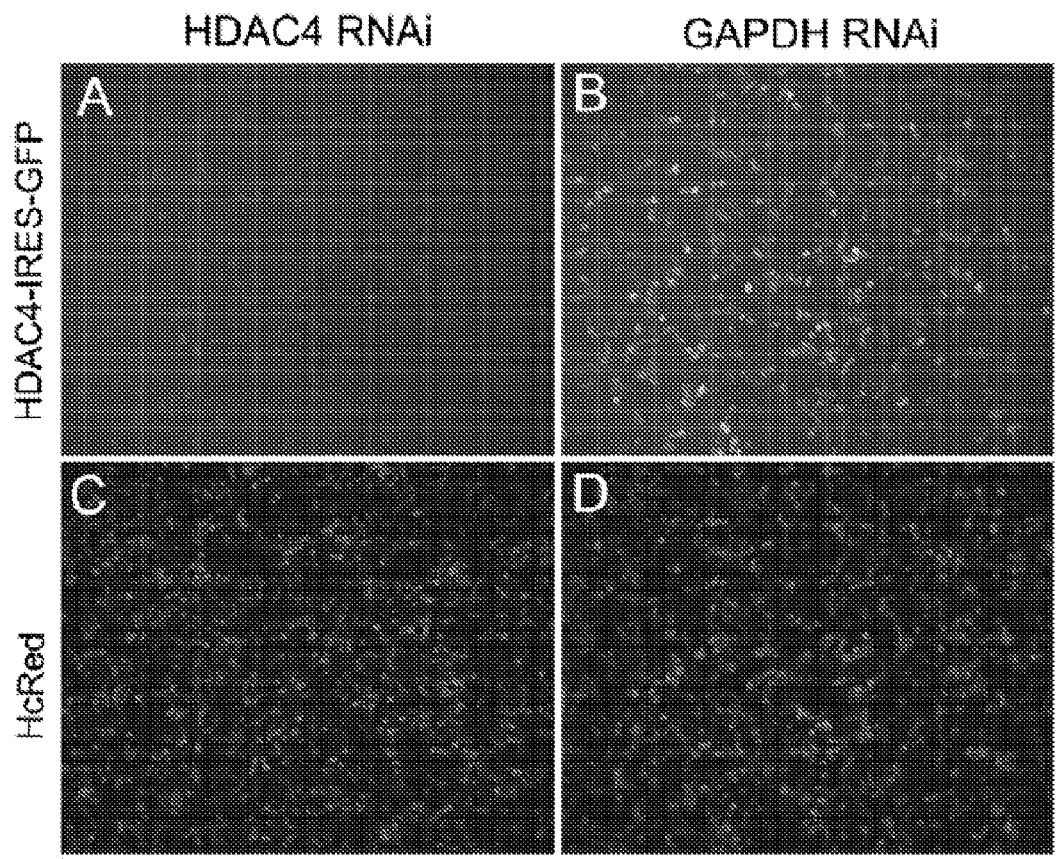
FIGS. 6A-6D depict an HDAC4 RNAi screen in transfected 293T cells. HDAC4 sensor HDAC4-IRES-GFP was co-transfected with either shRNA to HDAC4 or shRNA to GAPDH into 293T cells. HDAC4 sensor knockdown was assayed 24 hours post-transfection. pCAG-HcRed was co-transfected to monitor the transfection efficiency. (A) HDAC4-IRES-GFP was knocked down by HDAC4 RNAi and not by GAPDH RNAi (B), while a comparable number of cells were transfected (C, D).

To investigate the function of HDAC4 in vivo, a plasmid with a shRNA directed against HDAC4 (FIG. 6) was electroporated into the P0 mouse retina by in vivo electroporation (Matsuda and Cepko (4) *Proc. Natl. Acad. Sci. USA* 101:16). To label transfected cells, a plasmid, pCAG-GFP, encoding green fluorescent protein (GFP) driven by a broadly active promoter, CAG, was co-electroporated. An shRNA directed against GAPDH was used as a control for a successful RNA targeting event. Retinas electroporated with the GAPDH shRNA showed that the majority of electroporated cells were rod photoreceptors, with a minority being BP cells, AC, and microglia (MG), located in the INL ((Id.) and FIG. 2A). When HDAC4 was targeted, the number of GFP+ cells declined rapidly (FIG. 2K) with very few seen at P6 (FIG. 2B), and no GFP+ cells were seen at P8 or later. The loss of GFP+ cells indicated that HDAC4 was required for survival. The RNAi phenotype observed was not due to an off-target effect as a co-electroporated pCAG vector expressing an allele of HDAC4 that is resistant to HDAC4 shRNA led to the appearance of as many GFP+ cells as the GAPDH control (FIG. 2C).

To further investigate if the HDAC4 shRNA led to cell death, a TUNEL assay was performed at P5. Many TUNEL+ cells were detected in the regions electroporated with the shRNA against HDAC4 (FIG. 2E). In the non-electroporated regions (FIG. 2F) of the same HDAC4 shRNA electroporated retina (FIG. 2E), very few TUNEL+ cells were observed, similar to the number observed in the GAPDH shRNA control (FIG. 2D). Only a small percentage of TUNEL+ cells showed GFP expression (arrowheads, FIG. 2E). Without intending to be bound by scientific theory, this observation may have been due to the fact that TUNEL detects only those cells undergoing the final phase of apoptosis. To detect an earlier phase of the apoptotic cascade, caspase activation was assayed. P5 retinal sections were stained with an antibody recognizing the activated (cleaved) form of caspase-3, an executing caspase active before DNA cleavage. A greater number of cells with activated caspase-3 staining were seen in the HDAC4 RNAi samples (FIG. 2J) compared to the GAPDH RNAi control (FIGS. 2G, 2I). Most activated caspase-3+ cells in the HDAC4 RNAi retina were GFP+ (arrows, FIG. 2H). On average, 6.5±1.6 cells (per 100 μm section) were scored activated caspase-3+ for HDAC4 RNAi, compared to 0.28±0.07 cells for GAPDH RNAi, using retinas from three independent experiments.

Overexpression of HDAC4 was accomplished by in vivo electroporation of pCAG-HDAC4 into the P0 mouse retina. Electroporated retinas were collected at P14 when retinal neurogenesis was complete (Young (1985) *Anat. Rec.* 212:199). In the control pCAG-GFP electroporation (FIG. 3A) more than 80% of the GFP+ cells became photoreceptors in the ONL, and about 10% of the GFP+ cells became BP cells in the upper half of the INL (Matsuda and Cepko (2004) *Proc. Natl. Acad. Sci. USA* 101:16)). However, when HDAC4 was overexpressed (FIG. 3B), more GFP+ cells were observed in the INL in the area occupied by BP cells, and they extended processes into the IPL. During retinal development, BP cells are overproduced, with many eliminated by P14 (Young (1984) Anat. Rec. 212:199).

TUNEL assay and immunohistochemistry and fluorescence microscopy were performed as previously described (Chen and Cepko (2007) *BMC Dev. Biol.* 7:78). Fluorescence images of retinal sections were processed using the LEICA TCS SP2 confocal microscope. Fluorescence images of flat-mount retinas were processed using Nikon ECLIPSE E1000 microscope. The following primary antibodies were used: HDAC4 (Sigma; stock was diluted 1:200 for use); blocking peptide for HDAC4, MSSQSHPDGLSGRDQPVEL (SEQ ID NO:3). was used at 0.1 μg/μl; Rho4D2 for rhodopsin ((MacKenzie (1983) *Biochemistry* 22:653) stock was diluted 1:100 for use); activated caspase-3 (Cell Signaling, stock was diluted 1:200 for use); and HIF1α (R&D Systems, stock was diluted 1:300 for use).

Example II

HDAC Expression Improved Photoreceptor Cell Survival

Figure 4:
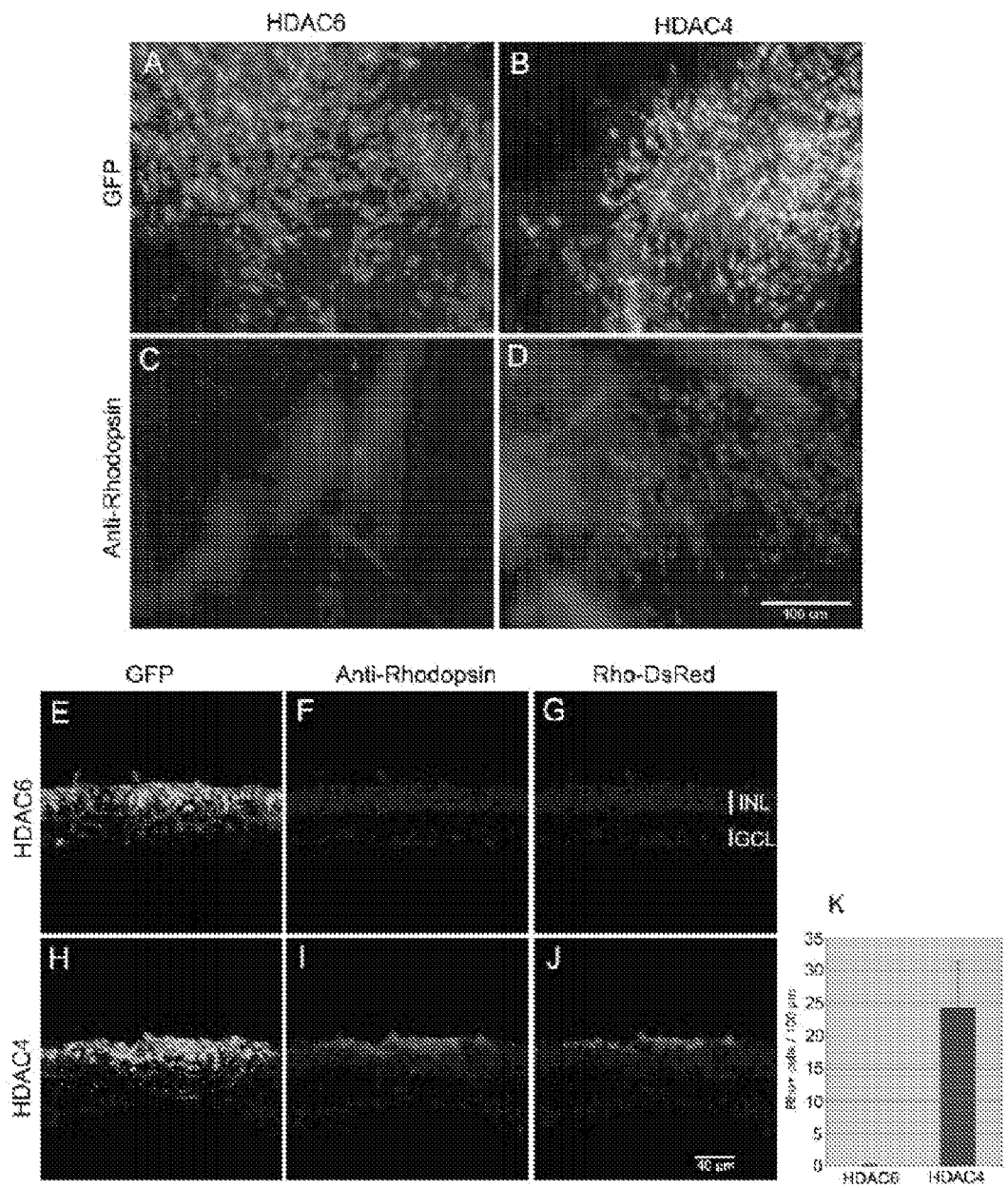
FIGS. 4A-4K illustrate that HDAC4 prevents retinal degeneration. (A-D) rd1 retinas were electroporated at P0 with pCAG-GFP and pCAG-HDAC4 (B,D), or pCAG-HDAC6 (A,C), and assayed at P50 for rod photoreceptor survival using anti-rhodopsin on flat-mount retinas (medium gray in C and D). GFP marks area of electroporation (light and medium gray in A and B) (E-J). Co-electroporation of pCAG-GFP and pCAG-HDAC6 (E, F, G) or pCAG-HDAC4 (H, I, J) and a reporter construct for the rhodopsin promoter (Rho-DsRed (11) at P0 with assay at P70 for anti-rhodopsin (F, I) or reporter activity. (K) Quantification of HDAC4 mediated rescue in rd1 mice at P70. The number of Rho-DsRed+ cells was counted per 100 µm section in electroporated areas. Five retinas were scored from three independent electroporations.
Figure 7:
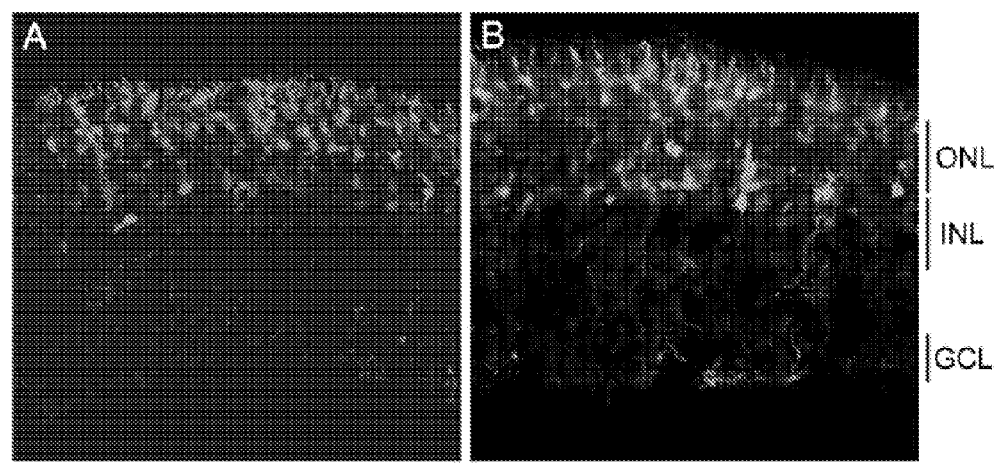
FIGS. 7A-7B depict that HDAC6 overexpression rescues BP cells from naturally occurring cell death in the wild-type retina. P14 cryosections from retinas electroporated at P0 by pCAG-GFP (A) or pCAG-HDAC6 (B), with BP cells located in the upper half of the INL.

Expression of HDAC4 by electroporation inhibited rod photoreceptor death. Electroporation of mouse retina at P0 results in transduction of many rods, but few cones (Matsuda and Cepko (2004) *Proc. Natl. Acad. Sci. USA* 101:16). Electroporation of pCAG-HDAC4 or pCAG-HDAC6 into P0 retinas was carried out. HDAC6 was included for a test of specificity, and because it recently has been shown to rescue retinal degeneration in *Drosophila* (Zhao et al. (2001) *J. Biol. Chem.* 276:35042). Retinas were collected at P50, a time point well beyond the time when rods have died in the control, untreated rd1 retinas. Flat-mounted retinas were stained with an antibody against rhodopsin, a rod-specific marker. In the transfected areas labeled by co-electroporated pCAG-GFP (FIGS. 4A, B), many rods were saved by HDAC4 (FIG. 4D), but not by HDAC6 (FIG. 4C). As an additional assay for the presence of rods, the activity of the rhodopsin promoter was assayed using a reporter plasmid for rhodopsin, Rho-DsRed (Matsuda and Cepko (2004) *Proc. Natl. Acad. Sci. USA* 101:16), in which a 2.2 kb rhodopsin promoter drives the expression of DsRed, a red fluorescence protein. Rho-DsRed was co-electroporated with pCAG-HDAC4 into the P0 rd1 retina. Tissue harvested at P70 showed that rods, marked by anti-rhodopsin immunohistochemistry (FIG. 4I), expressed the rhodopsin promoter (FIG. 4J) in the GFP-labeled electroporated area (FIG. 4H). The HDAC6-electroporated retina (FIG. 4E), did not exhibit rhodopsin immunoreactive cells (FIG. 4F) nor rhodopsin promoter activity (FIG. 4G). On average, 24.3±7.2 rhodopsin+ cells were scored per 100 μm section for HDAC4 treated retinas and 0 rhodopsin+ cells were seen in the HDAC6 electroporated retinas (FIG. 4K) or in the non-electroporated areas of the HDAC4 treated retinas. HDAC6 did not rescue diseased rod photoreceptor death. However, HDAC6 was as potent as HDAC4 in protecting bipolar cells from naturally occurring cell death in the rd1 retina (FIGS. 4E, 4H), as well as in the wild-type retina (FIG. 7).

Survival of cone photoreceptors depends upon the survival of rod photoreceptors; therefore it was possible that HDAC4 treated retinas would also have more cone photoreceptors. HDAC4 electroporated retinas (FIG. 4O) were collected at P70 and stained with peanut agglutinin (PNA), which labels cones. HDAC4 clearly increased cone density (FIG. 4Q) in the area with rescued rods (FIG. 4P), compared with HDAC6 electroporated retinas (FIGS. 4L-4N). The increased cone density was seen only in the HDAC4 electroporated area (FIGS. 4R-4T).

Example III

Overexpressed Cytoplasmic HDAC Prevented Rod Photoreceptor Cell Loss

HDAC4 was found predominantly in the cytoplasm in wild-type murine photoreceptors. (FIGS. 1B, 4U, 4X). The effect of cytoplasmic HDAC4 on photoreceptor survival effect was tested. HDAC4-L175A is a cytoplasmic mutant that does not interact with MEF2 transcription factors and therefore stays in the cytoplasm. A nuclear-localized mutant, HDAC-3SA, was also tested. HDAC-3SA mutant has its three serine phosphorylation sites mutated to alanine, which causes the mutant to stay in the nucleus (Vega et al. (2004) *Cell* 119:555; Zhao et al. (2001) *J. Biol. Chem.* 276:35042). Each of these alleles was electroporated into the rd1 mouse retina at P0 and rod photoreceptor survival was assayed by anti-rhodopsin immunohistochemistry. The cytoplasmic HDAC4-L175A mutant preserved rd1 rods out to at least P70 (FIGS. 4V, 4Y). The nuclear HDAC4-3SA mutant failed to rescue even until P50 (FIGS. 4W, 4Z). Thus, cytoplasmic HDAC4-L175A was effective at preventing rod photoreceptor cell loss.

Example IV

HIF1α Protein and Retinal Cell Degeneration

Figure 5:
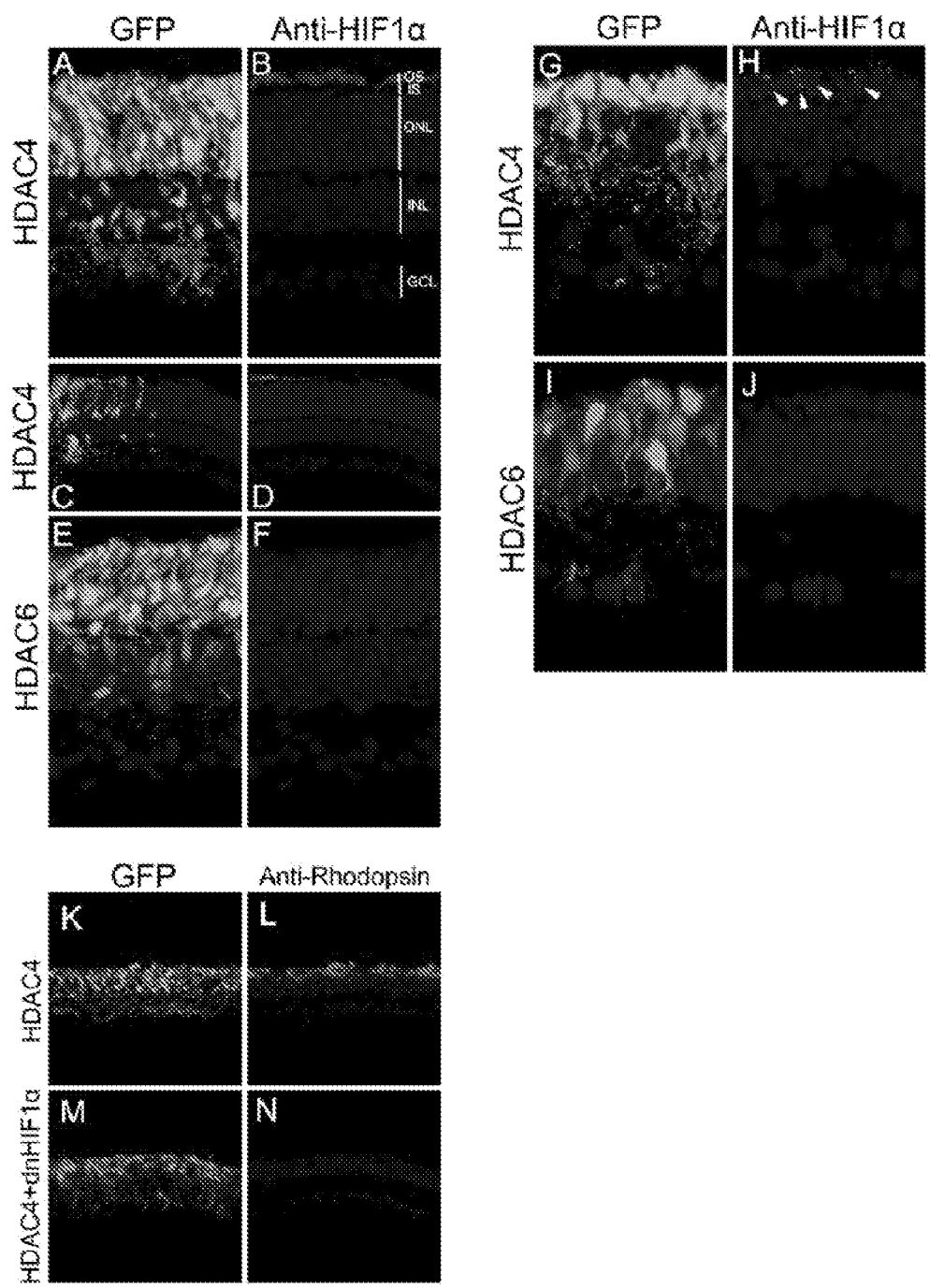
FIGS. 5A-5N illustrate that HDAC4 stabilized the HIF1α protein, and HIF1α was required for photoreceptor rescue by HDAC4. (A-F) HDAC4 stabilized HIF1α in the wild-type retina. Wild-type retinas were electroporated at P0 with pCAG-HDAC4 and pCAG-GFP, or pCAG-HDAC6 and pCAG-GFP, and assayed at P14 by anti-HIF1α immunohistochemistry on retinal sections. (A) In the HDAC4 electroporated retina, HIF1α protein was detected in the photoreceptor OS by anti-HIF1α (B), only in the HDAC4 electroporated area (C, D). (E) In the HDAC6 electroporated area, no HIF1α immunreactivity (F) was detected. (G-J) HDAC4 stabilized HIF1α in the rd1 retina. rd1 retinas were co-electroporated at P0 with pCAG-HDAC4 and pCAG-GFP (G, H), or pCAG-HDAC6 and pCAG-GFP (I, J), and assayed at P22 by anti-HIF1α immunohistochemistry. (K-N) Stabilized HIF1α was required for rescue of photoreceptors by HDAC4. rd1 retinas were co-electroporated at P0 with pCAG-HDAC4 (K,L) or pCAG-HDAC4 plus a dominant negative (dn) version of HIF1α, pCAG-dnHIF1α (M, N), and pCAG-GFP, and assayed at P70 for rod photoreceptor survival by rhodopsin immunohistochemistry.

HIF1α protein plays a central role in the regulation of oxygen homeostasis (Semenza (2000) *J. Appl. Physiol.* 88:1474; Semenza (2006) *Exp. Physiol.* 91:803) and is involved in the activation of genes involved in metabolism, angiogenesis, erythropoiesis, glycolysis, cardiovascular development and systemic $O_2$ homeostasis (GENEATLAS). HIF1α protein is not detectable in the mature mouse retina under normal conditions. Hypoxia preconditioning stabilizes HIF1α and protects photoreceptors from light-induced retinal degeneration (Grimm et al. (2002) *Nat. Med.* 8:718). HIF1α protein stability is regulated by lysine acetylation. Acetylation of HIF1α by the acetyl-transferase, ARD1, enhances its ubiquitination and proteasomal degradation (Jeong et al. (2002) *Cell* 111:709). To test if HDACs could stabilize HIF1α, HDAC4 and HDAC6 were each electroporated at P0 into the wild-type or rd1 retina. Immunohistochemistry for HIF1α was carried out on the mature retina. HIF1α protein was detected in the OS of wild-type photoreceptors (FIGS. 5A, 5B), but only in the electroporated areas (FIGS. 5C, 5D). No HIF1α immunoreactivity was detected following HDAC6 electroporation (FIGS. 5E, 5F). Likewise, HDAC4, but not HDAC6 (FIGS. 5I, 5J), led to HIF1α protein that appeared nuclear/perinuclear in the photoreceptors of the rd1 retina (FIGS. 5G, 5H).

To investigate whether HIF1α was required for the HDAC4-mediated photoreceptor rescue in rd1 mice, a dominant negative HIF1α (dnHIF1α) construct (Jiang et al. (1996) *J. Biol. Chem.* 271:17771) was co-electroporated with pCAG-HDAC4 into the rd1 retina at P0, and photoreceptor survival was monitored by anti-rhodopsin at P70. While HDAC4 alone resulted in the preservation of photoreceptors (FIGS. 5K, 5L), dnHIF1α negated the photoreceptor survival effect of HDAC4 (FIGS. 5M, 5N).

Figure 8:
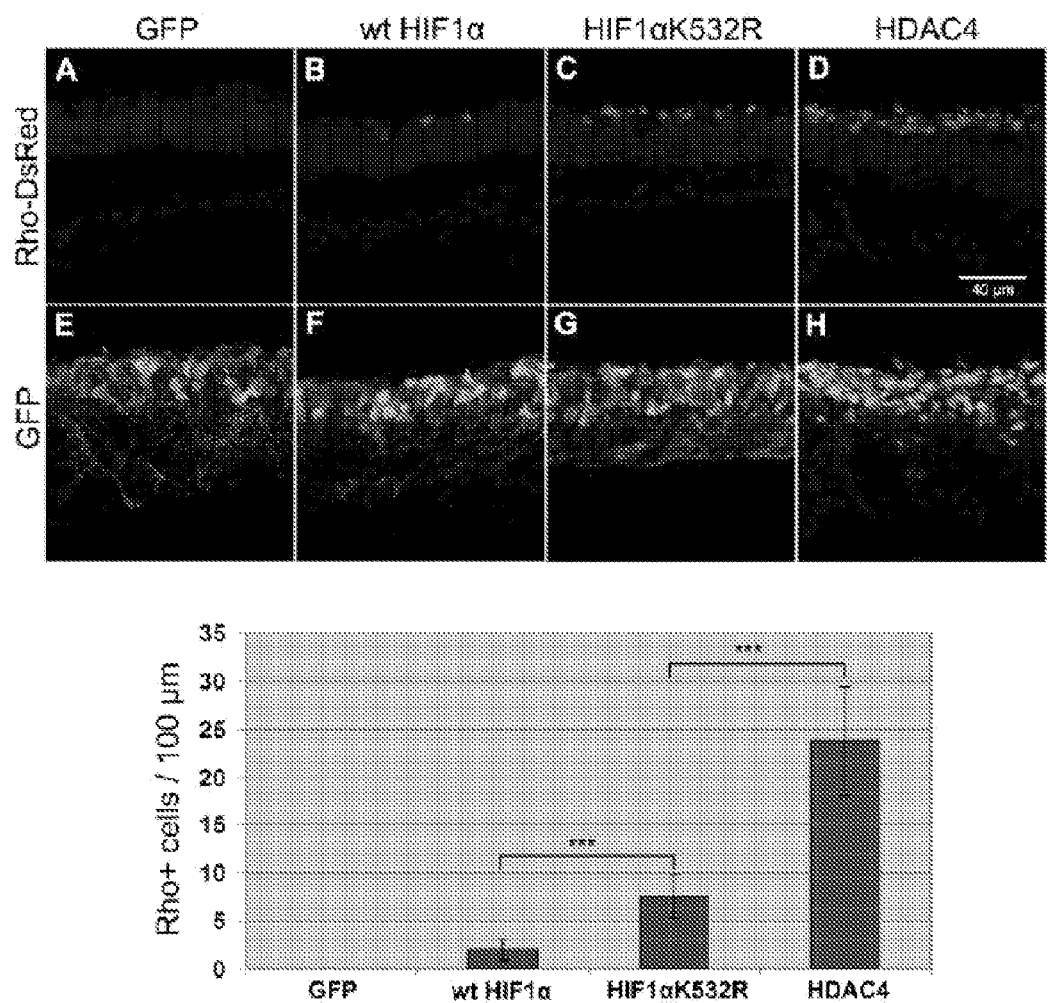
FIGS. 8A-8I depict that HIF1α acetylation mutant rescues retinal degeneration. (A-H) rd1 retinas were electroporated at P0 with pCAG-GFP, Rho-DsRed and pCAG-wt HIF1α (B, F), pCAG-HIF1αK532R(C, G) or pCAG-HDAC4 (D, H), and assayed at P70 for rod photoreceptor survival. (I) Quantification of photoreceptor survival in rd1 mice at P70. The number of Rho-DsRed+ cells was counted per 100 µm section in electroporated areas. Three retinas were scored for each treatment. *** p<0.05 by Student's t-Test.

To further investigate whether acetylation of HIF1α could play a role in rescuing rod cell death in the rd1 retina, HIF1αK532R, a constitutively active acetylation mutant of HIF1α that is more stable than its wild-type form (Jeong et al. (2002) *Cell* 111:709), and the wild-type HIF1α were tested by in vivo electroporation into the rd1 retina at P0. Rod photoreceptor survival was monitored by the co-electroporated Rho-DsRed at P70. The survival effects of HIF1α, HIF1αK532R, and HDAC4 were quantified by counting the number of Rho+ cells per 100 μm section (FIG. 8I). While no rods were detected with the control GFP electroporation (FIGS. 8A, 8E), wild-type HIF1α preserved a few rods (FIGS. 8B, 8F). HIF1αK532R saved more rods than did wild-type HIF1α (FIGS. 8C, 8G). HDAC4 was the most potent in saving rod photoreceptors (FIGS. 8D, 8H). Without intending to be bound by scientific theory, the greater potency of HDAC4 relative to HIF1αK532R might be due to HDAC4 having target(s) in addition to HIF1α, or it could be the case that HIF1αK532R is not as potent as the wild-type allele of HIF1α following HDAC4 mediated deacetylation.

Example V

Retrovirus-Mediated HDAC4 Expression Protected Retinal Cells from Cell Death

Figure 3:
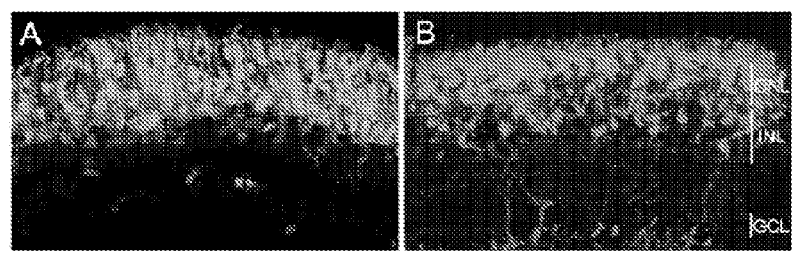
FIGS. 3A-3F illustrate that HDAC4 overexpression rescues bipolar (BP) cells from naturally occurring cell death. Cryosections from retinas electroporated by pCAG-GFP (A) or pCAG-HDAC4 (B), with BP cells located in the upper half of the INL and their processes extending to the IPL. (C) A schematic illustration showing how retinal clones would be shaped by naturally occurring BP death, and prevention of death by HDAC4. (D) Clonal analysis at P21 using replication-incompetent retrovirus LIA or LIA-HDAC4 injected at P0. LIA-HDAC4 clones exhibited an increase in the percentage of BP cell-containing clones, and a reduction in the percentage of one rod clones. 800-1000 clones were analyzed on each of 3 retinas infected by LIA or LIA-HDAC4. *** p<0.05 by Student's t-Test. (E) Retinal section showing a typical one rod clone that comprises the majority of the clone types. (F) Retinal section showing a typical one rod plus one BP clone that was the most increased clone type labeled by LIA-HDAC4.
Figure 3:
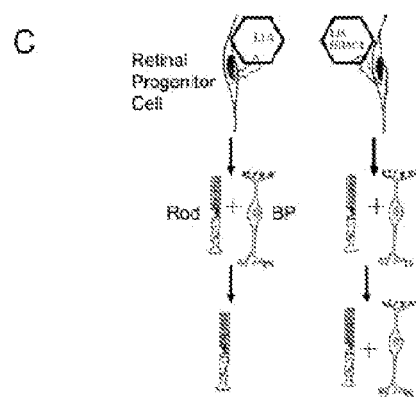
Figure 3:
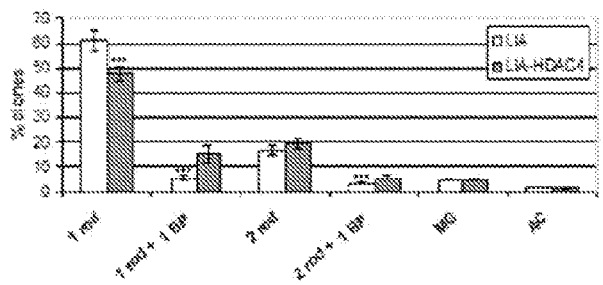
Figure 3:
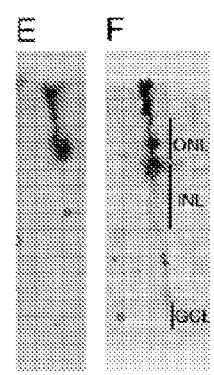

Retroviral lineage analysis was conducted to investigate whether elevated HDAC4 protein would preserve bipolar (BP) cells. As illustrated in FIG. 3C, previous lineage analyses showed that a P0 retinal progenitor can give rise to a rod photoreceptor and a BP cell, as well as many clones with only a single rod.

Many BP cells die naturally; therefore, it is likely that some rod-only clones result from loss of a BP cell from clones that initially have both a rod(s) and a BP cell. If HDAC4 expression can prevent bipolar cell death, infection with a lineage tracing retrovirus encoding HDAC4 should result in an increase in clones with BP cells, and a decrease in clones with a single rod. To test this hypothesis, clonal analysis was performed using a replication-incompetent retrovirus, LIA, expressing HDAC4. Analysis using replication-incompetent retrovirus LIA was performed as previously described (Cepko et al. (1998) *Curr. Top. Dev. Biol.* 36:51; Dyer, C. L. Cepko (2001) *J. Neurosci.* 21:4259). LIA retrovirus was made as described and had a titer of approximately $1\times10^7$ cfu/ml. Half a microliter viral suspension was injected into the subretinal space of the P0 mouse retina. Retinas were fixed at P21 and AP stained for cells generated from viral-infected retinal progenitors. Retinas were infected with the control LIA virus and virus containing the HDAC gene (LIA-HDAC4) at P0 in vivo. Tissue was collected at P21 and assayed for the number and types of cells in clones (FIG. 3D). Clones containing rod cells alone (FIG. 3E) decreased by approximately 13% from 61.2% for the control LIA infection to 47.9% for LIA-HDAC4 infection. At the same time, there was ~2-fold increase in the percentage of clones containing one rod plus one BP (FIG. 3F) for LIA-HDAC4 clones (14.9%), compared to 5.7% for LIA clones. There was also a statistically significant increase in the number of clones containing 2 rods plus 1 BP from 3.4% for LIA infection to 5.7% for LIA-HDAC4 infection. When the two categories, 1 rod plus 1 BP and 2 rods plus 1 BP, were added together, total BP containing clones increased from 9.1% for LIA infection to 20.6% for LIA-HDAC4 infection. These results are consistent with increased survival of BP cells and are complementary to the findings from the HDAC4 RNAi treatment, both of which are described further herein.

The following summarizes the results of Examples I-V.

Using the mouse retina as a model system to examine HDAC4 function in vivo, it was found that HDAC4 plays an essential role in neuronal survival. Reduction in HDAC4 by RNAi led to extensive apoptotic cell death through a caspase-3-activated pathway. HDAC4 overexpression saved BP cells from naturally occurring cell death. More importantly from a therapeutic perspective, HDAC4 rescued photoreceptor death in rd1 mice. Using alleles of HDAC4 that encoded proteins restricted to the cytoplasm or to the nucleus, the survival-promoting function of HDAC4 was shown to be mediated by cytoplasmic HDAC4. Although nuclear HDAC4 failed to rescue retinal degeneration, it led to increased AC production at the expense of other retinal cell types. These data indicate that HDAC4 has distinct functions in distinct cellular compartments.

HIF1α transcriptional activity was required for HDAC4-mediated rescue of photoreceptor degeneration in rd1 mice. Intriguingly, HDAC6 did not lead to an increase in HIF1α protein or promote rod survival in mice. Its rescue of degeneration in *Drosophila* was in a model of proteasome impairment, where HDAC6 was seen to be required for induction of autophagy (Pandey et al. (2007) *Nature* 447:859). Without intending to be bound by scientific theory, this function might be due to its distinct structural features that lead to its classification as a Class II, but not a Class IIa HDAC, while HDAC4 is a Class IIa HDAC (Yang and Gregoire (2005) *Mol. Cell. Biol.* 25:2873). Therefore, more than one pathway for neuronal survival is regulated by HDACs. As HDAC4 is expressed in the cytoplasm of neurons in other areas of the CNS (Bolger and Yao (2005) *J. Neurosci.* 25:9544), these data indicate that HDAC4 may be neuroprotective in other neurodegenerative diseases. In addition, HDAC inhibitors may be effective as anti-cancer therapeutic agents.

Example VI

As described above in Example III, it has been shown that the HDAC4 gene can be delivered to rod photoreceptors in vivo and suppress rod death, as well as cone death. The gene was delivered using electroporation, which resulted in rod transduction, but not cone transduction. This showed that HDAC4 could rescue rods through a process intrinsic to rods. The rescue of cones, however, was indirect, as the gene was not delivered to cones.

In humans, as well as animals, with retinitis pigmentosa (RP), the disease gene is only expressed in rods, yet, cone death follows rod death. Therefore, cone survival is due to the survival of neighboring rods. Promoting rod survival in RP should, thus, promote cone survival as shown by the electroporation experiments.

Since electroporation does not transduce all cells, and since it is not a stable method for long term transduction, an alternative means of gene transfer was developed. Viral vectors can produce broader and more stable transduction. Viral vectors also have the advantage of being able to transduce a wider range of species than electroporation.

Figure 10:
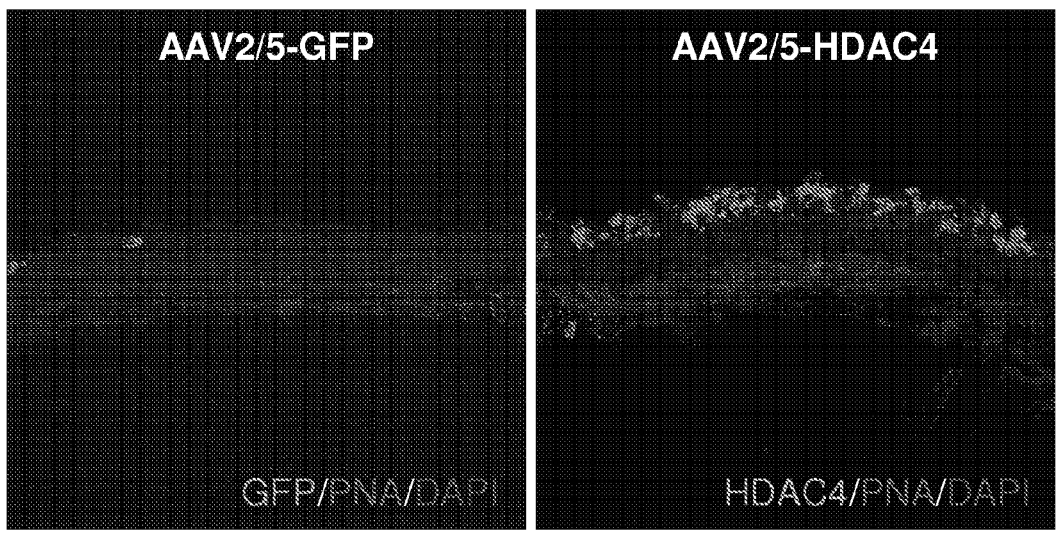
FIG. 10 depicts that injection of AAV2/5 HDAC4 leads to cone survival. AAV 2/5 encoding GFP (control) or HDAC4 were injected into the subretinal space of a P0 rd1 mouse eye. At P60, the retina was sectioned and stained immunohistochemically for HDAC4 (light gray) or a cone antigen (PNA, in medium gray). The nuclei were stained by DAPI. In the retina with AAV HDAC4, more cones survived, as revealed by the number of cells stained by both PNA and HDAC4. Very few cones survived in the control infection.

An adeno-associated virus (AAV) that transduces the HDAC4 gene was created. This is the AAV2/5 virus, which can infect photoreceptor cells. The CMV promoter and CAG promoters have been used to drive expression. The CMV promoter vector has been used to infect the rd1 mouse model of RP, at postnatal day 0 (P0). The results showed that it is capable of promoting cone survival, directly. The rods still died following infection due to the delay in the expression of HDAC4 from this vector. Typically, AAV2/5 with the CMV promoter does not express high levels of a viral gene until almost 4 weeks post infection. Since the rods die in the rd1 by P21, they would not be expected to survive. However, the cones die with much slower kinetics, beginning at about P21, and continuing into the periphery until about 3 months (P90), whereupon the majority of cones will have died. Infection with AAV2/5-HDAC4 led to the survival of many more cones, particularly in the central retina, until at least P60 (FIG. 10). Control viruses expressing only GFP did not show significant cone survival, particularly in the periphery by this age. (FIG. 10)

These data demonstrate that it possible to treat RP patients who have lost their rods, and are experiencing a loss of cone vision (i.e. daylight and color vision). Furthermore, since the death kinetics of rods are much slower in patients with RP, the rods will also survive using this method.

Example VII

As described above in Example VI, it has been shown that infection of rd1 photoreceptor cells with AAV2/5-HDAC4 led to cone survival until at least P60. However, due to the fast rate of rod death in this animal model and the delay in expression of HDAC4 from the AAV2/5 vector, the rods did not survive.

Therefore, in order to demonstrate that HDAC4 expression can also lead to rod survival, a mouse model of retinal degeneration with slower death kinetics of rods than the rd1 mouse model described above is used. For example, the rhodopsin knockout mouse (Rho−/−) is used.

The HDAC4 gene is expressed in a viral vector operably linked to a constituitive promoter. The construct is used to infect photoreceptor cells by electroporation, subretinal and/or intravitreal injection.

Based on the evidence presented herein, it is expected that the results will show that the construct is capable of promoting rod survival, directly.

What is claimed:

1. A method of inhibiting death of a retinal cell compromised by a neurodegenerative eye disorder, comprising administering to the retina of a subject having the neurodegenerative eye disorder an isolated HDAC4 nucleic acid molecule, thereby inhibiting death of the retinal cell.

2. A method for treating or preventing a neurodegenerative eye disorder in a subject, comprising administering to the retina of said subject an isolated HDAC4 nucleic acid molecule, thereby treating or preventing said neurodegenerative eye disorder in said subject.

3. A method of inhibiting death of an isolated retinal cell compromised by a neurodegenerative eye disorder, comprising contacting said isolated retinal cell with an isolated HDAC4 nucleic acid molecule, thereby inhibiting death of the isolated retinal cell.

4. The method of claim 1, wherein the HDAC4 nucleic acid molecule comprises a wild-type HDAC4 gene.

5. The method of claim 1, wherein the retinal cell is a photoreceptor cell.

6. The method of claim 5, wherein the photoreceptor cell is a rod cell.

7. The method of claim 5, wherein the photoreceptor cell is a cone cell.

8. The method of any one of claim 1, 2, or 3, wherein the retinal cell is selected from the group consisting of a bipolar cell, a rod photoreceptor cell and a cone photoreceptor cell.

9. The method of any one of claim 1, 2, or 3, wherein the nucleic acid molecule is expressed in the cytoplasm.

10. The method of claim 9, wherein the nucleic acid molecule comprises an HDAC4 gene comprising a mutation that causes the exogenous HDAC4 to be localized to the cytoplasm of the cell.

11. The method of claim 10, wherein the HDAC4 is HDAC4-L175A.

12. The method of claim 10, wherein the HDAC4 is HDAC4-4118.

13. The method of any one of claim 1, 2, or 3, wherein the neurodegenerative eye disorder is age-related macular degeneration.

14. The method of any one of claim 1, 2, or 3, wherein the neurodegenerative eye disorder is retinitis pigmentosa.

15. The method of any one of claim 1, 2, or 3, wherein the nucleic acid molecule is contained within a vector.

16. The method of claim 15, wherein the vector is selected from the group consisting of a retrovirus vector, an adenovirus vector, an adenoviral/retroviral chimera vector, an adeno-associated virus (AAV) vector, a herpes simplex virus I or II vector, a parvovirus vector, a reticuloendotheliosis virus vector, a poliovirus vector, a papillomavirus vector, a vaccinia virus vector and a lentivirus vector.

17. The method of claim 16, wherein the vector is an AAV vector.

18. The method of claim 17, wherein the AAV vector is an AAV 2/5 or an AAV 2/8 vector.

19. A method of inhibiting death of a bipolar cell in a subject, comprising administering to the retina of said subject an isolated HDAC6 nucleic acid molecule, thereby inhibiting death of said bipolar cell.

20. A method of inhibiting death of an isolated bipolar cell, comprising contacting said isolated bipolar cell with an isolated HDAC6 nucleic acid molecule, thereby inhibiting death of said bipolar cell.

* * * * *

UNITED STATES PATENT AND TRADEMARK OFFICE
CERTIFICATE OF CORRECTION

PATENT NO. : 8,912,153 B2  
APPLICATION NO. : 13/058346  
DATED : December 16, 2014  
INVENTOR(S) : Constance L. Cepko et al.

Page 1 of 1

It is certified that error appears in the above-identified patent and that said Letters Patent is hereby corrected as shown below:

In the Specification

At Column 1, Line numbers 12-14, delete "This invention was made with government support under EY09676 awarded by the National Institutes of Health. The United States Government has certain rights in the invention.", replace it with -- This invention was made with government support under EY009676 awarded by National Institutes of Health (NIH). The government has certain rights in this invention --

Signed and Sealed this  
Twenty-seventh Day of September, 2022

Katherine Kelly Vidal  
*Director of the United States Patent and Trademark Office*